(12) United States Patent
Li et al.

(10) Patent No.: US 10,508,269 B2
(45) Date of Patent: Dec. 17, 2019

(54) POLYPEPTIDE HAVING A POLYESTER DEGRADING ACTIVITY AND USES THEREOF

(71) Applicants: CARBIOS, Saint-Beauzire (FR); CENTRE NATIONAL DE LA RECHERCHE SCIENTIFIQUE, Paris (FR); UNIVERSITE DE POITIERS, Poitiers (FR)

(72) Inventors: Luen-Luen Li, Vertaizon (FR); Thierry Ferreira, Iteuil (FR); Willy Aucher, Poitiers (FR); Steven Colas, Reims (FR); Linette Lionelle Kadri, Poitiers (FR)

(73) Assignees: CARBIOS, Saint-Beauzire (FR); CENTRE NATIONAL DE LA RECHERCHE SCIENTIFIQUE, Paris (FR); UNIVERSITE DE POITIERS, Poitiers (FR)

(*) Notice: Subject to any disclaimer, the term of this patent is extended or adjusted under 35 U.S.C. 154(b) by 113 days.

(21) Appl. No.: 15/556,655

(22) PCT Filed: Mar. 11, 2016

(86) PCT No.: PCT/EP2016/055348
§ 371 (c)(1),
(2) Date: Sep. 8, 2017

(87) PCT Pub. No.: WO2016/146540
PCT Pub. Date: Sep. 22, 2016

(65) Prior Publication Data
US 2018/0051264 A1 Feb. 22, 2018

(30) Foreign Application Priority Data
Mar. 13, 2015 (EP) .................................. 15159061

(51) Int. Cl.
| | | |
|---|---|---|
| *C12N 9/16* | (2006.01) | |
| *C12N 15/00* | (2006.01) | |
| *C12N 1/20* | (2006.01) | |
| *C12P 7/62* | (2006.01) | |
| *C12P 7/42* | (2006.01) | |
| *C12P 21/06* | (2006.01) | |
| *C12P 21/04* | (2006.01) | |
| *C07H 21/04* | (2006.01) | |
| *C12N 9/18* | (2006.01) | |
| *C08J 11/10* | (2006.01) | |
| *C12P 7/56* | (2006.01) | |

(52) U.S. Cl.
CPC .............. *C12N 9/18* (2013.01); *C08J 11/105* (2013.01); *C12N 15/00* (2013.01); *C12P 7/42* (2013.01); *C12P 7/56* (2013.01); *C12P 7/625* (2013.01)

(58) Field of Classification Search
None
See application file for complete search history.

(56) References Cited

U.S. PATENT DOCUMENTS

| | | |
|---|---|---|
| 5,032,512 A | 7/1991 | Witholt et al. |
| 5,145,779 A | 9/1992 | Pometto et al. |
| 5,212,219 A | 5/1993 | Griffin |
| 5,316,847 A | 5/1994 | Suominen |
| 5,378,738 A | 1/1995 | Deguchi et al. |
| 5,426,047 A | 6/1995 | Ito et al. |
| 6,312,578 B1 | 11/2001 | Canivenc et al. |
| 6,429,006 B1 | 8/2002 | Porro et al. |
| 7,465,575 B2 | 12/2008 | Nilsson |
| 7,534,597 B2 | 5/2009 | Hause et al. |
| 7,960,154 B1 | 6/2011 | Nakajima et al. |
| 8,137,953 B2 | 3/2012 | Miller et al. |
| 8,476,056 B2 | 7/2013 | Hoang et al. |
| 8,614,076 B2 | 12/2013 | Wada et al. |
| 8,859,260 B2 | 10/2014 | Sawai et al. |
| 9,476,073 B2 | 10/2016 | Boisart |
| 9,528,132 B2 | 12/2016 | Mazzoli et al. |
| 10,124,512 B2 | 11/2018 | Boisart et al. |
| 2005/0261465 A1 | 11/2005 | Nagarajan |
| 2006/0106120 A1 | 5/2006 | Abe et al. |
| 2011/0008855 A1 | 1/2011 | Park et al. |
| 2011/0200771 A1 | 8/2011 | Barclay |
| 2011/0245057 A1 | 10/2011 | Scoledes et al. |
| 2011/0319588 A1 | 12/2011 | Coupin et al. |
| 2012/0184005 A1 | 7/2012 | Ferreira et al. |
| 2013/0274373 A1 | 10/2013 | Yoshikawa et al. |
| 2014/0303278 A1 | 10/2014 | Ferreira et al. |
| 2015/0056673 A1 | 2/2015 | Boisart |
| 2015/0290840 A1 | 10/2015 | Boisart et al. |

(Continued)

FOREIGN PATENT DOCUMENTS

| | | |
|---|---|---|
| CN | 101 457 218 | 6/2009 |
| CN | 102250379 | 11/2011 |

(Continued)

OTHER PUBLICATIONS

Written Opinion in International Application No. PCT/EP2017/062028, dated Jun. 30, 2017, pp. 1-5.

(Continued)

*Primary Examiner* — Yong D Pak
(74) *Attorney, Agent, or Firm* — Saliwanchik, Lloyd & Eisenschenk

(57) ABSTRACT

The present invention relates to a new isolated polypeptide comprising an amino acid sequence having at least 75%, 80%, 85%, 90%, 95%, 99% or 100% identity to the full length amino acid sequence set forth in SEQ ID NO:1, and having a polyester degrading activity, and uses thereof.

21 Claims, 8 Drawing Sheets
Specification includes a Sequence Listing.

(56) References Cited

U.S. PATENT DOCUMENTS

| | | |
|---|---|---|
| 2016/0280881 A1 | 9/2016 | Boisart et al. |
| 2017/0114205 A1 | 4/2017 | Maille |
| 2017/0313998 A1 | 11/2017 | Alvarez et al. |
| 2017/0349723 A1 | 12/2017 | Ferreira et al. |
| 2018/0142097 A1 | 5/2018 | Guemard et al. |
| 2018/0186943 A1 | 7/2018 | Chateau et al. |

FOREIGN PATENT DOCUMENTS

| | | |
|---|---|---|
| CN | 102675712 | 9/2012 |
| CN | 103980535 | 8/2014 |
| EP | 0 421 413 | 4/1991 |
| EP | 0 738 752 | 10/1996 |
| EP | 1 548 053 | 6/2005 |
| EP | 2 013 280 | 1/2009 |
| EP | 2 348 122 | 7/2011 |
| EP | 2 377 945 | 10/2011 |
| EP | 2 471 910 | 7/2012 |
| EP | 2 626 386 | 8/2013 |
| JP | 2000-506442 | 5/2000 |
| JP | 2002-293982 | 10/2002 |
| JP | 2002-320499 | 11/2002 |
| JP | 2002 362578 | 12/2002 |
| JP | 2003-079388 | 3/2003 |
| JP | 2003-128835 | 5/2003 |
| JP | 2004 058010 | 2/2004 |
| JP | 2004-290130 | 10/2004 |
| JP | 2004 292705 | 10/2004 |
| JP | 2007 319092 | 12/2007 |
| JP | 2012 149273 | 8/2012 |
| JP | 2012-152171 | 8/2012 |
| JP | 2013 000099 | 1/2013 |
| JP | 5 630597 | 11/2014 |
| KR | 20110045975 | 5/2011 |
| WO | WO 89/10381 | 11/1989 |
| WO | WO 2005/026245 | 3/2005 |
| WO | WO 2010/012805 | 2/2010 |
| WO | WO 2010/081887 | 7/2010 |
| WO | WO 2011/039489 | 4/2011 |
| WO | WO 2013/144239 | 10/2013 |
| WO | WO 2014/079844 | 5/2014 |
| WO | WO 2014/122698 | 8/2014 |
| WO | WO 2014/167518 | 10/2014 |
| WO | WO 2014/167562 | 10/2014 |
| WO | WO 2015/067619 | 5/2015 |
| WO | WO 2015/097104 | 7/2015 |
| WO | WO 2015/173265 | 11/2015 |
| WO | WO 2016/198650 | 12/2016 |
| WO | WO 2016/198652 | 12/2016 |
| WO | WO 2017/108577 | 6/2017 |
| WO | WO 2017/198786 | 11/2017 |

OTHER PUBLICATIONS

Database WPI, Accession No. 2009-K99963, Jun. 17, 2009, pp. 1-2, XP-002690934.

Database WPI, Accession No. 2008-F66138, Dec. 13, 2007, pp. 1-2, XP-002690935.

Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.

Petrov, K. et al. "$_L$(+)-Lactic acid production from starch by a novel amylolytic *Lactococcus lactis* subsp. *lactis* 884" *Food Microbiology*, Jun. 2008, pp. 550-557, vol. 25.

Currently pending claims of U.S. Appl. No. 14/443,524, 2016, pp. 1-4.

Bernard, N. et al. "Cloning of the D-lactate dehydrogenase gene from *Lactobacillus delbrueckii* subsp. *bulgaricus* by complementation in *Escherichia coli*" *FEBS*, Sep. 1991, pp. 61-64, No. 1.

Wieczorek, A. et al. "Engineering the cell surface display of cohesins for assembly of cellulosome-inspired enzyme complexes on *Lactococcus lactis*" *Microbial Cell Factories*, Sep. 2010, pp. 1-13, Vo. 9, No. 69.

Wieczorek, A. et al. "Effects of synthetic cohesin-containing scaffold protein architecture on binding dockerin-enzyme fusions on the surface of *Lactococcus lactis*" *Microbial Cell Factories*, 2012, pp. 1-13, vol. 160, No. 11.

Koukiekolo, R. et al. "Degradation of Corn Fiber by *Clostridium cellulovorans* Cellulases and Hemicellulases and Contribution of Scaffolding Protein CbpA" Applied and Environmental Microbiology, Jul. 1, 2005, pp. 3504-3511, vol. 71, No. 7.

Cha, J. et al. "Effect of Multiple Copies of Cohesins on Cellulase and Hemicellulase Activities of *Clostridium cellulovorans* Mini-cellulosomes" *Journal of Microbiology and Biotechnology*, 2007, pp. 1782-1788, vol. 17, No. 11.

Kataeva, I. et al. "Interaction between *Clostridium thermocellum* endoglucanase CelD and polypeptides derived from the cellulosome-integrating protein CipA: stoichiometry and cellulolytic activity of the complexes" *Biochemical Journal*, 1997, pp. 617-624, vol. 326, No. 2.

Wen, F. et al. "Yeast Surface Display of Trifunctional Minicellulosomes for Simultaneous Saccharification and Fermentation of Cellulose to Ethanol" Applied and Environmental Microbiology, Feb. 1, 2010, pp. 1251-1260, vol. 76, No. 4.

Hyeon, J. E. et al. "Production of minicellulosomes for the enhanced hydrolysis of cellulosic substrates by recombinant *Corynebacterium glutamicum*" Enzyme and Microbial Technology, 2011, pp. 371-377, vol. 48.

Sun, J. et al. "Direct Conversion of Xylan to Ethanol by Recombinant *Saccharomyces cerevisiae* Strains Displaying an Engineered Minihemicellulosome" Applied and Environmental Microbiology, Jun. 2012, pp. 3837-3845, vol. 78, No. 11.

Database EMBL [Online] Accession No. HC441374, "Sequence 9 from Patent WO2010012805" Feb. 20, 2010, pp. 1-3, XP-002697306.

Database Geneseq [Online] Accession No. AZM34659, "*Clostridium* sp. Cellulose-binding protein-A (CbpA) DNA SEQ: 6" Oct. 13, 2011, p. 1, XP-002697307.

Written Opinion in International Application No. PCT/EP2013/061413, dated Aug. 5, 2013, pp. 1-7.

Devos, D. et al. "Practical Limits of Function Prediction" *Proteins: Structure, Function and Genetics*, 2000, pp. 98-107, vol. 41.

Whisstock, J. C. et al. "Prediction of protein function from protein sequence and structure" *Quarterly Reviews of Biophysics*, 2003, pp. 307-340, vol. 36, No. 3.

Witkowski, A. et al. "Conversion of a β-Ketoacyl Synthase to a Malonyl Decarboxylase by Replacement of the Active-Site Cysteine with Glutamine" *Biochemistry*, 1999, pp. 11643-11650, vol. 38.

Kisselev, L. "Polypeptide Release Factors in Prokaryotes and Eukaryotes: Same Function, Different Structure" *Structure*, Jan. 2002, pp. 8-9, vol. 10.

Database WPI, Accession No. 2005-262580, Mar. 24, 2005, pp. 1-3, XP-002690554.

Database WPI, Accession No. 2004-751104, Oct. 21, 2004, pp. 1-2, XP-002690555.

Currently pending claims of U.S. Appl. No. 14/387,285, 2014, pp. 1-3.

Yoshida, S. et al. "A bacterium that degrades and assimilates poly(ethylene terephthalate)" *Science*, Mar. 11, 2016, pp. 1196-1199, vol. 351.

Demirel, B. et al. "Crystallization Behavior of PET Materials" *BAU Fen Bil. Enst. Dergisi Cilt*, 2011, pp. 26-35, vol. 13, No. 1.

Kyrikou, I. et al. "Biodegradation of Agricultural Plastic Films: A Critical review" *J Polym Environ*, 2007, pp. 125-150, vol. 15.

Chen, S. et al. "Identification and Characterization of Bacterial Cutinase" *The Journal of Biological Chemistry*, Sep. 19, 2008, pp. 25854-25862, vol. 238, No. 38.

Ronkvist, A. M. et al. "Cutinase-Catalyzed Hydrolysis of Poly(ethylene terephthalate)" *Macromolecules*, 2009, pp. 5128-5138, vol. 42.

Nabil, H. et al. "Recycled Polyethylene Terephthalate Filled Natural Rubber Compounds: Effects of Filler Loading and Types of Matrix" *Journal of Elastomers and Plastics*, 2011, pp. 1-21, vol. 00-2011.

Bartolome, L. et al. "Recent Developments in the Chemical Recycling of PET" Material Recycling—Trends and Perspectives, Mar. 16, 2012, pp. 1-21.

(56) References Cited

OTHER PUBLICATIONS

Arutchelvi, J. et al. "Biodegradation of polyethylene and polypropylene" *Indian Journal of Biotechnology*, Jan. 2008, pp. 9-22, vol. 7.

Iwamoto, A. et al. "Enzymatic degradation of plastics containing polycaprolactone" *Polymer Degradation and Stability*, Jan. 1, 1994, pp. 205-213, vol. 45.

Mueller, R.-J. "Biological degradation of synthetic polyesters—Enzymes as potential catalysts for polyester recycling" *Process Biochemistry*, 2006, pp. 2124-2128, vol. 41, No. 10.

Written Opinion in International Application No. PCT/EP2014/073742, dated Aug. 8, 2015, pp. 1-5.

Herrero Acero, E. et al. "Enzymatic Surface Hydrolysis of PET: Effect of Structural Diversity on Kinetic Properties of Cutinases from *Thermobifida*" *Macromolecules*, 2011, pp. 4632-4640, vol. 44, No. 12.

Herrero Acero, E. et al. "Surface Engineering of a Cutinase From *Thermobifida cellulosilytica* for Improved Polyester Hydrolysis" *Biotechnology & Bioengineering*, Oct. 2013, pp. 2581-2590, vol. 110, No. 10.

Shah, A. A. et al. "Degradation of aliphatic and aliphatic-aromatic co-polyesters by depolymerases from *Roseateles depolymerans* strain TB-87 and analysis of degradation products by LC-MS" *Polymer Degradation and Stability*, Oct. 16, 2013, pp. 2722-2729, vol. 98, No. 12.

Written Opinion in International Application No. PCT/EP2015/060521, dated Jul. 20, 2015, pp. 1-6.

Wikipedia, https://web.archive.org/web/20130424032652/https://en.wikipedia.org/wiki/Polyethylene_terephthalate, archived Apr. 24, 2013, accessed Aug. 13, 2018, pp. 1-13.

Sukkhum, S. et al. "A novel poly ($_L$-lactide) degrading actinomycetes isolated from Thai forest soil, phylogenic relationship and the enzyme characterization" *The Journal of General and Applied Microbiology*, 2009, pp. 459-467, vol. 55, No. 6.

Sukkhum, S. et al. "Poly($_L$-Lactide)-Degrading Enzyme Production by *Actinomadura keratinilytica* T16-1 in 3 L Airlift Bioreactor and Its Degradation Ability for Biological Recycle" *Journal of Microbiology and Biotechnology*, Jan. 28, 2012, pp. 92-99, vol. 22, No. 1.

Written Opinion in International Application No. PCT/EP2015/074222, dated Feb. 1, 2016, pp. 1-5.

Niaounakis, 2013. Chapter 4: Disposal. Biopolymers Reuse, Recycling, and Disposal. A Volume in Plastics Design Library, a PDL Handbook Series. ISBN 978-1-4557-3145-9, published by Elsevier Inc, pp. 107-150.

Sugimori, Mar., 2013. Protease, washing agent containing the protease, and method of manufacturing the washing agent. EMBL AB809463, pp. 1-2.

Albertsson, A- C. et al. "Chemistry and biochemistry of polymer biodegradation" *Chemistry and Technology of Biodegradable Polymers*, Jan. 1, 1994, pp. 7-17, Section 2.

Database WPI [Online] Accession No. 2012-Q50933, Sep. 9, 2012, p. 1, XP-002740253.

Database WPI [Online] Accession No. 2004-046313, May 8, 2003, pp. 1-2, XP-002740254.

Written Opinion in International Application No. PCT/EP2015/080557, dated Feb. 3, 2016, pp. 1-6.

Written Opinion in International Application No. PCT/EP2016/063369, dated Aug. 1, 2016, pp. 1-6.

Written Opinion in International Application No. PCT/EP2016/063373, dated Aug. 8, 2017, pp. 1-7.

Okino, S. et al. "Production of D-lactic acid by *Corynebacterium glutamicum* under oxygen deprivation" *Applied Microbiology and Biotechnology*, Jan. 10, 2008, pp. 449-454, vol. 78, No. 3.

Database WPI [Online] Accession No. 2012-K88398, Jan. 27, 2011, pp. 1-2, XP-002759107.

Written Opinion in International Application No. PCT/EP2016/081205, dated Jun. 1, 2017, pp. 1-19.

Currently pending claims of U.S. Appl. No. 16/302,107, 2018, pp. 1-4.

Currently pending claims of U.S. Appl. No. 16/064,494, 2018, pp. 1-3.

Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 1, 2003, pp. 2498-2504, vol. 69, No. 5.

Gouda, M. K. et al. "Production of a Polyester Degrading Extracellular Hydrolase from *Thermomonospora fusca*" *Biotechnology Progress*, Sep. 2002, pp. 927-934, vol. 18, No. 5.

Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 1, 2005, pp. 7333-7340, vol. 187, No. 21.

Oda, Y. et al. "Degradation of Polylactide by Commercial Proteases" *Journal of Polymers and the Environment*, Jan. 2000, pp. 29-32, vol. 8, No. 1.

Written Opinion in International Application No. PCT/EP2016/055348, dated Jun. 2, 2016, pp. 1-6.

Database UniProt [Online] Accession No. I0LED3, Jun. 13, 2012, pp. 1-2, XP-002743807.

Database Geneseq [Online] Accession No. BAJ28992, Jan. 31, 2013, pp. 1-10, XP-002743803.

Database Geneseq [Online] Accession No. BAJ28991, Jan. 31, 2013, pp. 1-2, XP-002743804.

Database UniProt [Online] Accession No. F4F956, Jun. 28, 2011, pp. 1-2, XP-002743805.

Database UniProt [Online] Accession No. A8LWF7, Dec. 4, 2007, p. 1-2, XP-002743806.

Claims as filed for U.S. Appl. No. 16/302,107, 2018, pp. 1-4.
Claims as filed for U.S. Appl. No. 16/317,160, 2019, pp. 1-3.
Claims as filed for U.S. Appl. No. 16/317,178, 2019, pp. 1-3.

```
ProtK  ------MRLSVLLSL-------------LPLALGAPAVEQRSEAAPLIEARGEMVANKYI
Japan  MSDVSVPRRRALRALAVTAAAAALAAAASTPALAAPTGDIR------YAGAPDAISGSYL
M2     ---MGLPRRSVLVGVA----ALAMVATATPAMAAEPVGTIR------AAGGATAVADSYI
              *   .* .:              . *.   *        .    :: .*:

ProtK  VKFKEGSALSAL------------DAAMEKISGKPDHVYKNVFSGFAATLDENMVRVLRA
Japan  VVLKGDAVGAANSRAARTAVPDRAATLAKRYGGSVGTVWSAALTGYSAKMSPAQARRLAA
M2     VVFKDSSV-------ARSSVGDTAQRLVGRHGGAVARTYGAALRGFEVRVDARAAARIAA
       *  :*   :.             :  .*     .:  .: *: . :.   . : *

ProtK  HPDVEYIEQDAVVTINAAQTN-APWGLARISSTSPGTSTYYYDESAGQGSCVYVIDTGIE
Japan  DPAVAYVEQDRVVTTQGTQTG-ATWGLDRIDQRNLPLNGTYTYPNTASNVRAYIIDTGIR
M2     DPAVAYVEQNHTVSISGTQTNPPSWGLDRIDQRALPLNSSYTYPNTASNVHAYIIDTGIR
       .* * *:**: .*:  ..:**   *** **..    . *   .:..   .*:*****.

ProtK  ASHPEFEGRAQMVKTYY--YSSRDGNGHGTHCAGTVGSRTYGVAKKTQLFGVKVLDDNGS
Japan  TTHSDFGGRASWGTNTVDSN-NTDCNGHGTHVAGTVGGNTYGVAKAVRLIAVKVLNCSGS
M2     FSHSDFGGRAVSGYDAVDGGSADDCNGHGTHVAGTVGGSAYGVAKGVQLVGVRVLNCQGS
        :*  :*  ***        *  ****** *****. :***** .:*..*:**: .**

ProtK  GQYSTIIAGMDFVASDKNNRNCPKGVVASLSLGGGYSSSVNSAAARLQSSGVMVAVAAGN
Japan  GSTTGVVSGVNWVTSN-----AVKPAVANMSLGGGASTTLDNAVANSIASGVTYAIAAGN
M2     GTNAGVIGGVDWVTAN-----AVKPAVANMSLGGGANASLDTAVRNSINSGVSYGLAAGN
       *   :  ::.*:::*:::       . *  .**.:*****  .::::.*. .    *** .:****

ProtK  N-NADARNYSPASEPSVCTVGASDRYDRRSSFSNYGSVLDIFGPGTSILSTWIGG--STR
Japan  S-SANACNYSPARVASAITVGATTSTDARASYSNYGSCLDIFAPGSSITSDWSTSDTATN
M2     DSGANACNTSPARTAEGITVGSTTNTDARSSFSNIGTCVDIFAPGSSITSAWHTNDTSTN
       .  *:* * ***    . ***::   * *:*:** *: :***.**:** * *      :*.

ProtK  SISGTSMATPHVAGLAAYLMTLGKTTA-ASACRYIADTANKGDLSNIPFGTVNLLAYNNY
Japan  TISGTSMATPHVAGAAALVLSANPSYTPAQVTSYLTTNSTASKVTNPGSGSPNRLLFVVN
M2     TISGTSMATPHVVGAAALVASANPAWTPQQVRDYLVNNATSNVVGNPGTGSPNKLLYVVN
       :***********.* ** : :      : :  .. *:. .:    : *   *: * * :

ProtK  QA----------------------------------------------------------
Japan  ------------------------------------------------------------
M2     GDTPPPTDDFSVSVSPTSGSTAPGGSVTATVGTATTNGSAQSVSLSASGLPSGATASFSP ProtK  ------------------------------------------------------------
Japan  ------------------------------------------------------------
M2     ATVTSGGSSTLTVSTSASTPPGTYSVTVTGTAASGSRTATYSLTVTGTGGGSCSGTNGTD ProtK  ------------------------------------------------------------
Japan  ------------------------------------------------------------
M2     VAIPDTGVTASSSIVISGCARNASSASTVAVNIVHTYRGDVVIDLVAPDGSSYRLKNSSL ProtK  --------------------------------------------
Japan  --------------------------------------------
M2     FDGADNINATYTANLSSEAANGTWQLRVRDVYTGDTGYLNTWTLTL
                                         Auxiliary polypeptide
```

FIGURE 3

1: Before 0.2 μm membrane filtration
2: After 0.2 μm membrane filtration
3: Retaining liquid in the tubing after 0.2 μm membrane filtration
4: After 30 kDa membrane filtration: < 30 kDa fraction
5: After 30 kDa membrane filtration: > 30 kDa

SEQUENCE LISTING

<160> NUMBER OF SEQ ID NOS: 10

<210> SEQ ID NO 1
<211> LENGTH: 395
<212> TYPE: PRT
<213> ORGANISM: micromonospora sp.

<400> SEQUENCE: 1

Met Gly Leu Pro Arg Arg Ser Val Leu Val Gly Val Ala Ala Leu Ala
1               5                   10                  15

Met Val Ala Thr Ala Thr Pro Ala Met Ala Ala Glu Pro Val Gly Thr
            20                  25                  30

Ile Arg Ala Ala Gly Gly Ala Thr Ala Val Ala Asp Ser Tyr Ile Val
        35                  40                  45

Val Phe Lys Asp Ser Ser Val Ala Arg Ser Ser Val Gly Asp Thr Ala
    50                  55                  60

Gln Arg Leu Val Gly Arg His Gly Gly Ala Val Ala Arg Thr Tyr Gly
65                  70                  75                  80

Ala Ala Leu Arg Gly Phe Glu Val Arg Val Asp Ala Arg Ala Ala Ala
            85                  90                  95

Arg Ile Ala Ala Asp Pro Ala Val Ala Tyr Val Glu Gln Asn His Thr
        100                 105                 110

Val Ser Ile Ser Gly Thr Gln Thr Asn Pro Pro Ser Trp Gly Leu Asp
    115                 120                 125

Arg Ile Asp Gln Arg Ala Leu Pro Leu Asn Ser Ser Tyr Thr Tyr Pro
130                 135                 140

Asn Thr Ala Ser Asn Val His Ala Tyr Ile Ile Asp Thr Gly Ile Arg
145                 150                 155                 160

Phe Ser His Ser Asp Phe Gly Gly Arg Ala Val Ser Gly Tyr Asp Ala
                165                 170                 175

Val Asp Gly Gly Ser Ala Asp Asp Cys Asn Gly His Gly Thr His Val
            180                 185                 190

Ala Gly Thr Val Gly Gly Ser Ala Tyr Gly Val Ala Lys Gly Val Gln
        195                 200                 205

Leu Val Gly Val Arg Val Leu Asn Cys Gln Gly Ser Gly Thr Asn Ala
    210                 215                 220

Gly Val Ile Gly Gly Val Asp Trp Val Thr Ala Asn Ala Val Lys Pro
225                 230                 235                 240

Ala Val Ala Asn Met Ser Leu Gly Gly Gly Ala Asn Ala Ser Leu Asp
                245                 250                 255

Thr Ala Val Arg Asn Ser Ile Asn Ser Gly Val Ser Tyr Gly Leu Ala
            260                 265                 270

Ala Gly Asn Asp Ser Gly Ala Asn Ala Cys Asn Thr Ser Pro Ala Arg
        275                 280                 285

Thr Ala Glu Gly Ile Thr Val Gly Ser Thr Thr Asn Thr Asp Ala Arg
    290                 295                 300

Ser Ser Phe Ser Asn Ile Gly Thr Cys Val Asp Ile Phe Ala Pro Gly
305                 310                 315                 320

Ser Ser Ile Thr Ser Ala Trp His Thr Asn Asp Thr Ser Thr Asn Thr
                325                 330                 335

Ile Ser Gly Thr Ser Met Ala Thr Pro His Val Val Gly Ala Ala Ala
            340                 345                 350

Leu Val Ala Ser Ala Asn Pro Ala Trp Thr Pro Gln Gln Val Arg Asp
        355                 360                 365

Tyr Leu Val Asn Asn Ala Thr Ser Asn Val Val Gly Asn Pro Gly Thr
    370                 375                 380

Gly Ser Pro Asn Lys Leu Leu Tyr Val Val Asn
385                 390                 395

<210> SEQ ID NO 2
<211> LENGTH: 1184
<212> TYPE: DNA
<213> ORGANISM: Micromonospora sp.

<400> SEQUENCE: 2
atgggtcttc cacgcaggtc cgtactcgtc ggggtggccg cgctggccat ggtgccaccc    60
gccacgcccg ccatggccgc cgaaccggtg ggcacgatcc gcgccgcggg cggcgccacg   120
gccgtggccg acagctacat cgtcgtcttc aaggacagct cggtcgcccg cagcagcgtc   180
gcgacaccgc gcagcggctg gtcggccggc acggcggcgc ggtcgcccgc acctacggcg   240

```
ccgccctgcg cggcttcgag gtccgggtcg acgccagggc cgccgcccgc atcgccgcgg      300
accccgccgt ggcgtacgtc gagcagaacc acacggtctc catcagcggc acccagacca      360
acccgccctc ctggggactg gaccggatcg accagcgggc cctgccgctg aacagctcct      420
acacgtaccc gaacacggcg agcaacgtgc acgcctacat catcgacacc ggcatccggt      480
tcagccacag cgacttcggc gggcgggccg tctccggcta cgacgccgtc gacggcggct      540
cggccgacga ctgcaacggg cacggcacgc acgtcgccgg caccgtcggc ggttcggcgt      600
acggcgtggc caagggcgtc cagctggtcg gcgtacgggt gctgaactgc agggcagcg       660 gcacgaacgc cggcgtcatc ggcggcgtcg actgggtgac cgccaacgcg gtcaagcccg      720
ccgtggccaa catgagcctc ggcggcggcg cgaacgcctc gctcgacacc gccgtgcgca      780
actccatcaa ctccggcgtg agctacggcc tggcggccgg caacgactcc ggcgccaacg      840
cctgcaacac ctcgcccgcc cggaccgccg agggcatcac cgtcggctcg acgaccaaca      900
ccgacgcgcg gtcgtcgttc tccaacatcg gcacctgcgt ggacatcttc gcgcccggct      960
cgtcgatcac ctcggcgtgg cacaccaacg acacctcgac caacacgatc agcggcacct     1020
cgatggcgac gccgcacgtg gtcggcgccg cggccctggt ggccagcgcc aacccggcct     1080
ggacgccgca gcaggtccgc gactacctgg tgaacaacgc caccagcaac gtggtgggca     1140
acccgggcac cggctcgccc aacaagctgc tctacgtcgt caac                      1184
```

<210> SEQ ID NO 3
<211> LENGTH: 226
<212> TYPE: PRT
<213> ORGANISM: Micromonospora sp.

<400> SEQUENCE: 3

```
Gly Asp Thr Pro Pro Thr Asp Asp Phe Ser Val Ser Val Ser Pro
1               5                   10                  15

Thr Ser Gly Ser Thr Ala Pro Gly Gly Ser Val Thr Ala Thr Val Gly
            20                  25                  30

Thr Ala Thr Asn Gly Ser Ala Gln Ser Val Ser Leu Ser Ala Ser
        35                  40                  45

Gly Leu Pro Ser Gly Ala Thr Ala Ser Phe Ser Pro Ala Thr Val Thr
    50                  55                  60

Ser Gly Gly Ser Ser Thr Leu Thr Val Ser Thr Ser Ala Ser Thr Pro
65                  70                  75                  80

Pro Gly Thr Tyr Ser Val Thr Val Thr Gly Thr Ala Ala Ser Gly Ser
                85                  90                  95

Arg Thr Ala Thr Tyr Ser Leu Thr Val Thr Gly Thr Gly Gly Ser
            100                 105                 110

Cys Ser Gly Thr Asn Gly Thr Asp Val Ala Ile Pro Asp Thr Gly Val
        115                 120                 125

Thr Ala Ser Ser Ser Ile Val Ile Ser Gly Cys Ala Arg Asn Ala Ser
    130                 135                 140

Ser Ala Ser Thr Val Ala Val Asn Ile Val His Thr Tyr Arg Gly Asp
145                 150                 155                 160

Val Val Ile Asp Leu Val Ala Pro Asp Gly Ser Ser Tyr Arg Leu Lys
                165                 170                 175

Asn Ser Ser Leu Phe Asp Gly Ala Asp Asn Ile Asn Ala Thr Tyr Thr
            180                 185                 190

Ala Asn Leu Ser Ser Glu Ala Ala Asn Gly Thr Trp Gln Leu Arg Val
        195                 200                 205
```

Arg Asp Val Tyr Thr Gly Asp Thr Gly Tyr Leu Asn Thr Trp Thr Leu
210                 215                 220

Thr Leu
225

<210> SEQ ID NO 4
<211> LENGTH: 678
<212> TYPE: DNA
<213> ORGANISM: Micromonospora sp.

<400> SEQUENCE: 4
ggcgacaccc cgccgccgac cgacgacttc tctgtctcgg tctcgccgac ctccggctcc     60
accgcgccgg gcggctcggt gaccgccacg gtcggcaccg ccacgaccaa cggctccgcc    120
cagtcggtga gcctctcggc cagcgggctg ccgtccgggg cgaccgcctc gttcagcccc    180
gccaccgtca cctcgggcgg ttcttcgacg ctgaccgtca gcacctcggc gagcacgccg    240
cccggcacct actccgtgac cgtgacgggc accgcgcct cgggcagcag gaccgccacc    300
tactcgctga cggtcaccgg caccggtggc ggcagctgct ccggcaccaa cggcaccgac    360
gtcgcgatcc cggacacggg cgtcacggcc agcagctcga tcgtgatctc cggctgtgcc    420
cgtaacgcct cgtcggcctc caccgtcgcg gtgaacatcg tgcacaccta ccgtggtgac    480
gtcgtcatcg acctggtcgc cccggacggc tcgtcctacc ggctgaagaa cagcagcctc    540
ttcgacggcg cggacaacat caacgccacc tacacggcga acctgtcgag cgaggcggcg    600
aacggcacct ggcagctgcg ggtgcgggac gtctacacgg gcgacaccgg ctacctgaac    660
acctggaccc tcaccctc                                                 678

<210> SEQ ID NO 5
<211> LENGTH: 620
<212> TYPE: PRT
<213> ORGANISM: Micromonospora

<400> SEQUENCE: 5

Gly Leu Pro Arg Arg Ser Val Leu Val Gly Val Ala Ala Leu Ala Met
1               5                   10                  15

Val Ala Thr Ala Thr Pro Ala Met Ala Ala Glu Pro Val Gly Thr Ile
                20                  25                  30

Arg Ala Ala Gly Gly Ala Thr Ala Val Ala Asp Ser Tyr Ile Val Val
            35                  40                  45

Phe Lys Asp Ser Ser Val Ala Arg Ser Val Gly Asp Thr Ala Gln
        50                  55                  60

Arg Leu Val Gly Arg His Gly Gly Ala Val Ala Arg Thr Tyr Gly Ala
65                  70                  75                  80

Ala Leu Arg Gly Phe Glu Val Arg Val Asp Ala Arg Ala Ala Arg
                85                  90                  95

Ile Ala Ala Asp Pro Ala Val Ala Tyr Val Glu Gln Asn His Thr Val
            100                 105                 110

Ser Ile Ser Gly Thr Gln Thr Asn Pro Pro Ser Trp Gly Leu Asp Arg
        115                 120                 125

Ile Asp Gln Arg Ala Leu Pro Leu Asn Ser Ser Tyr Thr Tyr Pro Asn
    130                 135                 140

Thr Ala Ser Asn Val His Ala Tyr Ile Ile Asp Thr Gly Ile Arg Phe
145                 150                 155                 160

Ser His Ser Asp Phe Gly Gly Arg Ala Val Ser Gly Tyr Asp Ala Val
                165                 170                 175

```
Asp Gly Gly Ser Ala Asp Asp Cys Asn Gly His Gly Thr His Val Ala
            180                 185                 190
Gly Thr Val Gly Gly Ser Ala Tyr Gly Val Ala Lys Gly Val Gln Leu
            195                 200                 205
Val Gly Val Arg Val Leu Asn Cys Gln Gly Ser Gly Thr Asn Ala Gly
            210                 215                 220
Val Ile Gly Gly Val Asp Trp Val Thr Ala Asn Ala Val Lys Pro Ala
225                 230                 235                 240
Val Ala Asn Met Ser Leu Gly Gly Gly Ala Asn Ala Ser Leu Asp Thr
                245                 250                 255
Ala Val Arg Asn Ser Ile Asn Ser Gly Val Ser Tyr Gly Leu Ala Ala
            260                 265                 270
Gly Asn Asp Ser Gly Ala Asn Ala Cys Asn Thr Ser Pro Ala Arg Thr
            275                 280                 285
Ala Glu Gly Ile Thr Val Gly Ser Thr Thr Asn Thr Asp Ala Arg Ser
            290                 295                 300
Ser Phe Ser Asn Ile Gly Thr Cys Val Asp Ile Phe Ala Pro Gly Ser
305                 310                 315                 320
Ser Ile Thr Ser Ala Trp His Thr Asn Asp Thr Ser Thr Asn Thr Ile
                325                 330                 335
Ser Gly Thr Ser Met Ala Thr Pro His Val Val Gly Ala Ala Ala Leu
            340                 345                 350
Val Ala Ser Ala Asn Pro Ala Trp Thr Pro Gln Gln Val Arg Asp Tyr
            355                 360                 365
Leu Val Asn Asn Ala Thr Ser Asn Val Val Gly Asn Pro Gly Thr Gly
            370                 375                 380
Ser Pro Asn Lys Leu Leu Tyr Val Val Asn Gly Asp Thr Pro Pro Pro
385                 390                 395                 400
Thr Asp Asp Phe Ser Val Ser Val Ser Pro Thr Ser Gly Ser Thr Ala
                405                 410                 415
Pro Gly Gly Ser Val Thr Ala Thr Val Gly Thr Ala Thr Thr Asn Gly
            420                 425                 430
Ser Ala Gln Ser Val Ser Leu Ser Ala Ser Gly Leu Pro Ser Gly Ala
            435                 440                 445
Thr Ala Ser Phe Ser Pro Ala Thr Val Thr Ser Gly Gly Ser Ser Thr
            450                 455                 460
Leu Thr Val Ser Thr Ser Ala Ser Thr Pro Pro Gly Thr Tyr Ser Val
465                 470                 475                 480
Thr Val Thr Gly Thr Ala Ala Ser Gly Ser Arg Thr Ala Thr Tyr Ser
                485                 490                 495
Leu Thr Val Thr Gly Thr Gly Gly Ser Cys Ser Gly Thr Asn Gly
            500                 505                 510
Thr Asp Val Ala Ile Pro Asp Thr Gly Val Thr Ala Ser Ser Ser Ile
            515                 520                 525
Val Ile Ser Gly Cys Ala Arg Asn Ala Ser Ser Ala Ser Thr Val Ala
            530                 535                 540
Val Asn Ile Val His Thr Tyr Arg Gly Asp Val Val Ile Asp Leu Val
545                 550                 555                 560
Ala Pro Asp Gly Ser Ser Tyr Arg Leu Lys Asn Ser Ser Leu Phe Asp
                565                 570                 575
Gly Ala Asp Asn Ile Asn Ala Thr Tyr Thr Ala Asn Leu Ser Ser Glu
            580                 585                 590
```

```
Ala Ala Asn Gly Thr Trp Gln Leu Arg Val Arg Asp Val Tyr Thr Gly
            595                 600                 605

Asp Thr Gly Tyr Leu Asn Thr Trp Thr Leu Thr Leu
    610                 615                 620

<210> SEQ ID NO 6
<211> LENGTH: 1866
<212> TYPE: DNA
<213> ORGANISM: Micromonospora sp.

<400> SEQUENCE: 6
atgggtcttc cacgcaggtc cgtactcgtc ggggtggccg cgctggccat ggtggccacc      60
gccacgcccg ccatggccgc cgaaccggtg ggcacgatcc gcgccgcggg cggcgccacg     120
gccgtggccg acagctacat cgtcgtcttc aaggacagct cggtcgcccg cagcagcgtc     180
ggcgacaccg cgcagcggct ggtcggccgg cacggcggcg cggtcgcccg cacctacggc     240
gccgccctgc gcggcttcga ggtcgggtc gacgccaggg ccgccgcccg catcgccgcg     300
gaccccgccg tggcgtacgt cgagcagaac cacacggtct ccatcagcgg cacccagacc     360
aacccgccct cctggggact ggaccggatc gaccagcggg ccctgccgct gaacagctcc     420
tacacgtacc cgaacacggc gagcaacgtg cacgcctaca tcatcgacac cggcatccgg     480
ttcagccaca gcgacttcgg cgggcgggcc gtctccggct acgacgccgt cgacggcggc     540
tcggccgacg actgcaacgg gcacggcacg cacgtcgccg cgaccgtcgg cggttcggcg     600
tacggcgtgg ccaagggcgt ccagctggtc ggcgtacggg tgctgaactg ccagggcagc     660
ggcacgaacg ccggcgtcat cggcggcgtc gactgggtga ccgccaacgc ggtcaagccc     720
gccgtggcca acatgagcct cggcggcggc gcgaacgcct cgctcgacac cgccgtgcgc     780
aactccatca actccggcgt gagctacggc ctggcggccg caacgactc cggcgccaac     840 gcctgcaaca cctcgcccgc ccggaccgcc gagggcatca ccgtcggctc gacgaccaac     900
accgacgcgc ggtcgtcgtt ctccaacatc ggcacctgcg tggacatctt cgcgcccggc     960
tcgtcgatca cctcggcgtg gcacaccaac gacacctcga ccaacacgat cagcggcacc    1020
tcgatggcga cgccgcacgt ggtcggcgcc gcggccctgg tggccagcgc caacccggcc    1080
tggacgccgc agcaggtccg cgactacctg gtgaacaacg ccaccagcaa cgtggtgggc    1140
aacccgggca ccggctcgcc caacaagctg ctctacgtcg tcaacggcga cacccccgccg    1200 ccgaccgacg acttctctgt ctcggtctcg ccgacctccg gctccaccgc gccgggcggc    1260
tcggtgaccg ccacggtcgg caccgccacg accaacggct ccgcccagtc ggtgagcctc    1320
tcggccagcg ggctgccgtc cggggcgacc gcctcgttca gccccgccac cgtcacctcg    1380
ggcggttctt cgacgctgac cgtcagcacc tcggcgagca cgccgcccgg cacctactcc    1440
gtgaccgtga cgggcaccgc ggcctcgggc agcaggaccg ccacctactc gctgacggtc    1500
accggcaccg gtggcggcag ctgctccggc accaacggca ccgacgtcgc gatcccggac    1560
acgggcgtca cggccagcag ctcgatcgtg atctccggct gtgcccgtaa cgcctcgtcg    1620
gcctccaccg tcgcggtgaa catcgtgcac acctaccgtg gtgacgtcgt catcgacctg    1680
gtcgccccgg acggctcgtc ctaccggctg aagaacagca gcctcttcga cggcgcggac    1740
aacatcaacg ccacctacac ggcgaacctg tcgagcgagg cggcgaacgg cacctggcag    1800
ctgcgggtgc gggacgtcta cacgggcgac accggctacc tgaacacctg gaccctcacc    1860
ctctga                                                                1866
```

<210> SEQ ID NO 7
<211> LENGTH: 1542
<212> TYPE: DNA
<213> ORGANISM: Micromonospora sp.

<400> SEQUENCE: 7

| | | | | | |
|---|---|---|---|---|---|
| ttgttggaga | gtttgatcct | ggctcaggac | gaacgctggc | ggcgtgctta | acacatgcaa | 60 |
| gtcgagcgga | aaggcccttc | ggggtactcg | agcggcgaac | gggtgagtaa | cacgtgagca | 120 |
| acctgcccta | ggctttggga | taaccccggg | aaaccggggc | taataccgaa | taggaccacc | 180 |
| ggtcgcatgg | ttggtggtgg | aaagttttc | ggcctgggat | gggctcgcgg | cctatcagct | 240 |
| tgttggtggg | gtgatggcct | accaaggcga | cgacgggtag | ccggcctgag | agggcgaccg | 300 |
| gccacactgg | gactgagaca | cggcccagac | tcctacggga | ggcagcagtg | gggaatattg | 360 |
| cacaatgggc | ggaagcctga | tgcagcgacg | ccgcgtgagg | gatgacggcc | ttcgggttgt | 420 |
| aaacctcttt | cagcagggac | gaagcgaaag | tgacggtacc | tgcagaagaa | gcgccggcca | 480 |
| actacgtgcc | agcagccgcg | gtaagacgta | gggcgcgagc | gttgtccgga | tttattgggc | 540 |
| gtaaagagct | cgtaggcggc | ttgtcgcgtc | gactgtgaaa | cccgcagct | caactgcggg | 600 |
| cctgcagtcg | atacgggcag | gctagagttc | ggtaggggag | actggaattc | ctggtgtagc | 660 |
| ggtgaaatgc | gcagatatca | ggaggaacac | cggtggcgaa | ggcgggtctc | tgggccgata | 720 |
| ctgacgctga | ggagcgaaag | cgtggggagc | gaacaggatt | agataccctg | gtagtccacg | 780 |
| ctgtaaacgt | tgggcgctag | gtgtgggggg | cctctccggt | tccctgtgcc | gcagctaacg | 840 |
| cattaagcgc | cccgcctggg | gagtacggcc | gcaaggctaa | aactcaaagg | aattgacggg | 900 |
| ggcccgcaca | agcggcggag | catgcggatt | aattcgatgc | aacgcgaaga | accttacctg | 960 |
| ggtttgacat | ggccgcaaaa | ctcgcagaga | tgtgaggtcc | ttcggggggcg | gtcacaggtg | 1020 |
| gtgcatggct | gtcgtcagct | cgtgtcgtga | gatgttgggt | taagtcccgc | aacgagcgca | 1080 |
| accctcgttc | gatgttgcca | gcgcgttatg | gcggggactc | atcgaagact | gccgggtca | 1140 |
| actcggagga | aggtggggat | gacgtcaagt | catcatgccc | cttatgtcca | gggcttcacg | 1200 |
| catgctacaa | tggccggtac | aatgggctgc | gataccgtga | ggtggagcga | atcccaaaaa | 1260 |
| gccggtctca | gttcggatcg | gggtctgcaa | ctcgacccccg | tgaagtcgga | gtcgctagta | 1320 |
| atcgcagatc | agcaacgctg | cggtgaatac | gttcccgggc | cttgtacaca | ccgcccgtca | 1380 |
| cgtcacgaaa | gtcggcaaca | cccgaagccg | gtgcccaac | ccttgtggag | ggagccgtcg | 1440 |
| aaggtggggc | tggcgattgg | gacgaagtcg | taacaaggta | gccgtaccgg | aaggtgcggc | 1500 |
| tggatcacct | cctttctaag | gagcaccttc | acccgaaagg | gt | | 1542 |

<210> SEQ ID NO 8
<211> LENGTH: 384
<212> TYPE: PRT
<213> ORGANISM: Parengyodontium album

<400> SEQUENCE: 8

Met Arg Leu Ser Val Leu Leu Ser Leu Leu Pro Leu Ala Leu Gly Ala
1               5                   10                  15

Pro Ala Val Glu Gln Arg Ser Glu Ala Ala Pro Leu Ile Glu Ala Arg
            20                  25                  30

Gly Glu Met Val Ala Asn Lys Tyr Ile Val Lys Phe Lys Glu Gly Ser
        35                  40                  45

Ala Leu Ser Ala Leu Asp Ala Ala Met Glu Lys Ile Ser Gly Lys Pro
    50                  55                  60

```
Asp His Val Tyr Lys Asn Val Phe Ser Gly Phe Ala Ala Thr Leu Asp
 65                  70                  75                  80

Glu Asn Met Val Arg Val Leu Arg Ala His Pro Asp Val Glu Tyr Ile
                 85                  90                  95

Glu Gln Asp Ala Val Val Thr Ile Asn Ala Ala Gln Thr Asn Ala Pro
            100                 105                 110

Trp Gly Leu Ala Arg Ile Ser Ser Thr Ser Pro Gly Thr Ser Thr Tyr
            115                 120                 125

Tyr Tyr Asp Glu Ser Ala Gly Gln Gly Ser Cys Val Tyr Val Ile Asp
            130                 135                 140

Thr Gly Ile Glu Ala Ser His Pro Glu Phe Glu Gly Arg Ala Gln Met
145                 150                 155                 160

Val Lys Thr Tyr Tyr Ser Ser Arg Asp Gly Asn Gly His Gly Thr
                165                 170                 175

His Cys Ala Gly Thr Val Gly Ser Arg Thr Tyr Gly Val Ala Lys Lys
                180                 185                 190

Thr Gln Leu Phe Gly Val Lys Val Leu Asp Asp Asn Gly Ser Gly Gln
            195                 200                 205

Tyr Ser Thr Ile Ile Ala Gly Met Asp Phe Val Ala Ser Asp Lys Asn
210                 215                 220

Asn Arg Asn Cys Pro Lys Gly Val Val Ala Ser Leu Ser Leu Gly Gly
225                 230                 235                 240

Gly Tyr Ser Ser Ser Val Asn Ser Ala Ala Ala Arg Leu Gln Ser Ser
                245                 250                 255

Gly Val Met Val Ala Val Ala Gly Asn Asn Asn Ala Asp Ala Arg
            260                 265                 270

Asn Tyr Ser Pro Ala Ser Glu Pro Ser Val Cys Thr Val Gly Ala Ser
            275                 280                 285

Asp Arg Tyr Asp Arg Arg Ser Ser Phe Ser Asn Tyr Gly Ser Val Leu
            290                 295                 300

Asp Ile Phe Gly Pro Gly Thr Ser Ile Leu Ser Thr Trp Ile Gly Gly
305                 310                 315                 320

Ser Thr Arg Ser Ile Ser Gly Thr Ser Met Ala Thr Pro His Val Ala
                325                 330                 335

Gly Leu Ala Ala Tyr Leu Met Thr Leu Gly Lys Thr Thr Ala Ala Ser
            340                 345                 350

Ala Cys Arg Tyr Ile Ala Asp Thr Ala Asn Lys Gly Asp Leu Ser Asn
            355                 360                 365

Ile Pro Phe Gly Thr Val Asn Leu Leu Ala Tyr Asn Asn Tyr Gln Ala
370                 375                 380

<210> SEQ ID NO 9
<211> LENGTH: 406
<212> TYPE: PRT
<213> ORGANISM: Micromonospora

<400> SEQUENCE: 9

Met Ser Asp Val Ser Val Pro Arg Arg Ala Leu Arg Ala Leu Ala
1               5                   10                  15

Val Thr Ala Ala Ala Ala Leu Ala Ala Ala Ser Thr Pro Ala
                20                  25                  30

Leu Ala Ala Pro Thr Gly Asp Ile Arg Tyr Ala Gly Ala Pro Asp Ala
            35                  40                  45

Ile Ser Gly Ser Tyr Leu Val Val Leu Lys Gly Asp Ala Val Gly Ala
50                  55                  60
```

Ala Asn Ser Arg Ala Ala Arg Thr Ala Val Pro Asp Arg Ala Thr
 65                  70                  75                  80

Leu Ala Lys Arg Tyr Gly Gly Ser Val Gly Thr Val Trp Ser Ala Ala
                 85                  90                  95

Leu Thr Gly Tyr Ser Ala Lys Met Ser Pro Ala Gln Ala Arg Arg Leu
            100                 105                 110

Ala Ala Asp Pro Ala Val Ala Tyr Val Glu Gln Asp Arg Val Val Thr
        115                 120                 125

Thr Gln Gly Thr Gln Thr Gly Ala Thr Trp Gly Leu Asp Arg Ile Asp
130                 135                 140

Gln Arg Asn Leu Pro Leu Asn Gly Thr Tyr Thr Tyr Pro Asn Thr Ala
145                 150                 155                 160

Ser Asn Val Arg Ala Tyr Ile Ile Asp Thr Gly Ile Arg Thr Thr His
                165                 170                 175

Ser Asp Phe Gly Gly Arg Ala Ser Trp Gly Thr Asn Thr Val Asp Ser
            180                 185                 190

Asn Asn Thr Asp Cys Asn Gly His Gly Thr His Val Ala Gly Thr Val
        195                 200                 205

Gly Gly Asn Thr Tyr Gly Val Ala Lys Ala Val Arg Leu Ile Ala Val
210                 215                 220

Lys Val Leu Asn Cys Ser Gly Ser Gly Ser Thr Thr Gly Val Val Ser
225                 230                 235                 240

Gly Val Asn Trp Val Thr Ser Asn Ala Val Lys Pro Ala Val Ala Asn
                245                 250                 255

Met Ser Leu Gly Gly Gly Ala Ser Thr Thr Leu Asp Asn Ala Val Ala
            260                 265                 270

Asn Ser Ile Ala Ser Gly Val Thr Tyr Ala Ile Ala Ala Gly Asn Ser
        275                 280                 285

Ser Ala Asn Ala Cys Asn Tyr Ser Pro Ala Arg Val Ala Ser Ala Ile
290                 295                 300

Thr Val Gly Ala Thr Thr Ser Thr Asp Ala Arg Ala Ser Tyr Ser Asn
305                 310                 315                 320

Tyr Gly Ser Cys Leu Asp Ile Phe Ala Pro Gly Ser Ser Ile Thr Ser
                325                 330                 335

Asp Trp Ser Thr Ser Asp Thr Ala Thr Asn Thr Ile Ser Gly Thr Ser
            340                 345                 350

Met Ala Thr Pro His Val Ala Gly Ala Ala Ala Leu Val Leu Ser Ala
        355                 360                 365

Asn Pro Ser Tyr Thr Pro Ala Gln Val Thr Ser Tyr Leu Thr Thr Asn
370                 375                 380

Ser Thr Ala Ser Lys Val Thr Asn Pro Gly Ser Gly Ser Pro Asn Arg
385                 390                 395                 400

Leu Leu Phe Val Val Asn
                405

<210> SEQ ID NO 10
<211> LENGTH: 621
<212> TYPE: PRT
<213> ORGANISM: Micromonospora

<400> SEQUENCE: 10

Met Gly Leu Pro Arg Arg Ser Val Leu Val Gly Val Ala Ala Leu Ala
1               5                   10                  15

Met Val Ala Thr Ala Thr Pro Ala Met Ala Ala Glu Pro Val Gly Thr

```
                    20                  25                  30
Ile Arg Ala Ala Gly Gly Ala Thr Ala Val Ala Asp Ser Tyr Ile Val
            35                  40                  45
Val Phe Lys Asp Ser Ser Val Ala Arg Ser Ser Val Gly Asp Thr Ala
        50                  55                  60
Gln Arg Leu Val Gly Arg His Gly Gly Ala Val Ala Arg Thr Tyr Gly
65                  70                  75                  80
Ala Ala Leu Arg Gly Phe Glu Val Arg Val Asp Ala Arg Ala Ala Ala
                85                  90                  95
Arg Ile Ala Ala Asp Pro Ala Val Ala Tyr Val Glu Gln Asn His Thr
            100                 105                 110
Val Ser Ile Ser Gly Thr Gln Thr Asn Pro Pro Ser Trp Gly Leu Asp
        115                 120                 125
Arg Ile Asp Gln Arg Ala Leu Pro Leu Asn Ser Ser Tyr Thr Tyr Pro
    130                 135                 140
Asn Thr Ala Ser Asn Val His Ala Tyr Ile Ile Asp Thr Gly Ile Arg
145                 150                 155                 160
Phe Ser His Ser Asp Phe Gly Gly Arg Ala Val Ser Gly Tyr Asp Ala
                165                 170                 175
Val Asp Gly Gly Ser Ala Asp Asp Cys Asn Gly His Gly Thr His Val
            180                 185                 190
Ala Gly Thr Val Gly Gly Ser Ala Tyr Gly Val Ala Lys Gly Val Gln
        195                 200                 205
Leu Val Gly Val Arg Val Leu Asn Cys Gln Gly Ser Gly Thr Asn Ala
    210                 215                 220
Gly Val Ile Gly Gly Val Asp Trp Val Thr Ala Asn Ala Val Lys Pro
225                 230                 235                 240
Ala Val Ala Asn Met Ser Leu Gly Gly Gly Ala Asn Ala Ser Leu Asp
                245                 250                 255
Thr Ala Val Arg Asn Ser Ile Asn Ser Gly Val Ser Tyr Gly Leu Ala
            260                 265                 270
Ala Gly Asn Asp Ser Gly Ala Asn Ala Cys Asn Thr Ser Pro Ala Arg
        275                 280                 285
Thr Ala Glu Gly Ile Thr Val Gly Ser Thr Thr Asn Thr Asp Ala Arg
    290                 295                 300
Ser Ser Phe Ser Asn Ile Gly Thr Cys Val Asp Ile Phe Ala Pro Gly
305                 310                 315                 320
Ser Ser Ile Thr Ser Ala Trp His Thr Asn Asp Thr Ser Thr Asn Thr
                325                 330                 335
Ile Ser Gly Thr Ser Met Ala Thr Pro His Val Val Gly Ala Ala Ala
            340                 345                 350
Leu Val Ala Ser Ala Asn Pro Ala Trp Thr Pro Gln Gln Val Arg Asp
        355                 360                 365
Tyr Leu Val Asn Asn Ala Thr Ser Asn Val Val Gly Asn Pro Gly Thr
    370                 375                 380
Gly Ser Pro Asn Lys Leu Leu Tyr Val Val Asn Gly Asp Thr Pro Pro
385                 390                 395                 400
Pro Thr Asp Asp Phe Ser Val Ser Val Ser Pro Thr Ser Gly Ser Thr
                405                 410                 415
Ala Pro Gly Gly Ser Val Thr Ala Thr Val Gly Thr Ala Thr Thr Asn
            420                 425                 430
Gly Ser Ala Gln Ser Val Ser Leu Ser Ala Ser Gly Leu Pro Ser Gly
        435                 440                 445
```

```
Ala Thr Ala Ser Phe Ser Pro Ala Thr Val Thr Ser Gly Gly Ser Ser
            450                 455                 460

Thr Leu Thr Val Ser Thr Ser Ala Ser Thr Pro Pro Gly Thr Tyr Ser
465                 470                 475                 480

Val Thr Val Thr Gly Thr Ala Ala Ser Gly Ser Arg Thr Ala Thr Tyr
                485                 490                 495

Ser Leu Thr Val Thr Gly Thr Gly Gly Ser Cys Ser Gly Thr Asn
                500                 505                 510

Gly Thr Asp Val Ala Ile Pro Asp Thr Gly Val Thr Ala Ser Ser Ser
            515                 520                 525

Ile Val Ile Ser Gly Cys Ala Arg Asn Ala Ser Ser Ala Ser Thr Val
            530                 535                 540

Ala Val Asn Ile Val His Thr Tyr Arg Gly Asp Val Val Ile Asp Leu
545                 550                 555                 560

Val Ala Pro Asp Gly Ser Ser Tyr Arg Leu Lys Asn Ser Ser Leu Phe
                565                 570                 575

Asp Gly Ala Asp Asn Ile Asn Ala Thr Tyr Thr Ala Asn Leu Ser Ser
                580                 585                 590

Glu Ala Ala Asn Gly Thr Trp Gln Leu Arg Val Arg Asp Val Tyr Thr
            595                 600                 605

Gly Asp Thr Gly Tyr Leu Asn Thr Trp Thr Leu Thr Leu
            610                 615                 620
```

POLYPEPTIDE HAVING A POLYESTER DEGRADING ACTIVITY AND USES THEREOF

CROSS-REFERENCE TO RELATED APPLICATION

This application is the U.S. national stage application of International Patent Application No. PCT/EP2016/055348, filed Mar. 11, 2016.

The Sequence Listing for this application is labeled "Seq-List-replace-2.txt" which was created on Aug. 26, 2019 and is 31 KB. The entire content of the sequence listing is incorporated herein by reference in its entirety.

FIELD OF THE INVENTION

The present invention relates to a novel polypeptide having a polyester degrading activity and the uses thereof for degrading polyester containing material, such as plastic products. The invention also relates to a novel isolated bacterial strain of the genus *Micromonospora* producing said polypeptide and to methods of producing said polypeptide. The invention further relates to plastic compounds containing said polypeptide and at least one polyester.

BACKGROUND OF THE INVENTION

Polyesters are used in a large number of technical fields, in particular in the form of plastic material, from food packaging to the medical field, via clothing and the automobile industry, etc. As an example, certain polyesters (for example polyethylene terephthalate—PET, polylactic acid—PLA, etc.) are used in the manufacture of clothes, carpets, but also in the form of a thermoset resin for the manufacture of packaging or automobile plastics or other parts.

As a consequence, the production of polyester containing plastics has increased dramatically over the last decades. More than 50% of these plastics are used for single-use disposable applications, such as packaging, agricultural films, disposable consumer items or for short-lived products that are discarded within a year of manufacture. Regrettably, plastics may persist for decades depending on local environmental factors, like levels of ultraviolet light exposure, temperature, presence of suitable microorganisms, etc. As a consequence, substantial quantities of plastics are piling up in landfill sites and in natural habitats worldwide, generating increasing environmental problems.

One solution to reduce environmental and economic impacts correlated to the accumulation of plastic is recycling wherein plastic material is mechanically reprocessed to manufacture new products. However, the actual recycling processes use huge amounts of electricity, particularly during the extruding step, and the equipment used is also expensive, leading to high prices which may be non-competitive compared to virgin plastic.

Another potential process for recycling plastic consists of chemical recycling allowing recovering the chemical constituents of the polymer. The resulting monomers may then be used to re-manufacture plastic or to make other synthetic chemicals. However, up to now, such recycling process has only been performed on purified polymers and is not efficient on raw plastic products constituted of a mix of crystallized and amorphous polymers and additives. Moreover, such recycling process is expensive leading to non-competitive monomers compared to virgin monomers.

On the other hand, enzymatic degradation is looked as an ideal waste treatment method because enzymes can accelerate hydrolysis of plastics and can be incorporated into a natural cycle of organic materials. Furthermore, the hydrolysate (i.e., monomers and oligomers) can be recycled as material for polymers. Thus, the depolymerization of polymers contained in a plastic product by enzymes is of great interest, as an alternative to the existing and unsatisfactory processes.

However, this enzymatic approach did not lead so far to the implementation of an effective and industrial enzymatic method of degrading polyester containing material.

Indeed, many bacteria are known to have the ability to degrade polyesters. For instance, regarding polylactic acid, there is a report of degrading enzymes derived from *Actinomycetes* such as *Amycolatopsis* sp. (strain K104-1) and from *Paenibacillus amylolyticus* (strain TB-13). However, up to now, the identified polypeptides have poor degrading ability and allow only degradation of the polymer in emulsion form. There are a limited number of reports on microorganisms capable of degrading polyester-containing material in film or pellet form, and their enzymes are poorly known. Furthermore, most of said identified polypeptides are efficient solely at elevated temperature. Their use thereby increases the cost of a thermal degradation process.

In view of the foregoing, there is a need for novel enzymes suitable for degrading polyesters and more particularly for degrading polyesters contained in plastic products.

SUMMARY OF THE INVENTION

Work conducted by the applicant has led to the identification of a novel polypeptide having a polyester degrading activity. This new polypeptide was first isolated from strains of bacteria of the genus *Micromonospora* sp. This polypeptide had never been reported or isolated in the art. The inventors have further shown that the unexpected and remarkable polyester degrading activity of said polypeptide may be efficiently used for degrading polyester containing material, such as plastic products. The inventors have further identified an auxiliary polypeptide that doesn't exhibit any degrading activity as such, but surprisingly shows capability to decrease the temperature at which an associated degrading enzyme is active. Said auxiliary polypeptide may also be used together with a degrading enzyme to increase polyester's degradation at low temperature.

Then, the invention stems inter alia from the identification of these new polypeptides having the remarkable properties of degrading polyester and/or optimizing polyester degradation. Based on these unexpected properties, the polypeptides of the invention may be successfully used for obtaining, even on an industrial scale, the degradation of polyesters contained in a plastic product.

It is therefore an object of the present invention to provide a polypeptide having a polyester degrading activity and comprising at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity.

It is a further object of the invention to provide a polypeptide having a polyester degrading activity and comprising at the C-terminal or N-terminal end an amino acid sequence having at least 75%, 80%, 85%, 90%, 95%, 99% or 100% identity to the full length amino acid sequence set forth in SEQ ID No3.

It is another object of the invention to provide an isolated bacterial strain of the genus *Micromonospora* expressing and optionally excreting a polypeptide as defined above.

Another object of this invention is a nucleic acid coding a polypeptide as defined above. The invention also relates to an expression cassette comprising a nucleic acid as defined above and to a vector comprising a nucleic acid or expression cassette as defined above.

The invention also relates to a recombinant cell, or host cell, preferably a recombinant microorganism, containing at least one nucleic acid or expression cassette or vector as defined above, and to extracts thereof that preferably exhibit the enzymatic activity.

The invention also relates to a method of producing the polypeptide of the invention, comprising (i) culturing a recombinant cell or a *Micromonospora* as defined above, (ii) recovering the culture supernatant, and optionally (iii) isolating or purifying the polypeptide.

The invention also provides a degrading composition comprising a polypeptide, a recombinant cell, a *Micromonospora* strain or an extract thereof, as defined above.

The invention further relates to the use of said polypeptide, degrading composition, recombinant cell, *Micromonospora* strain, or extract thereof for the degradation of a polyester containing material.

It is a further object of the invention to provide a method for degrading a polyester containing material, wherein a polyester containing material is contacted with a polypeptide, recombinant cell or *Micromonospora* strain, or extract thereof, or degrading composition as defined above.

The invention also relates to a method for producing monomers and/or oligomers from a polyester containing material, comprising exposing a polyester containing material to a polypeptide, degrading composition, recombinant cell or *Micromonospora* strain or extract thereof, as defined above, and optionally recovering monomers and/or oligomers.

The invention further relates to a plastic compound containing a polypeptide, recombinant cell, *Micromonospora* strain or extract thereof, as defined above, and at least one polyester.

LEGEND TO THE FIGURES

FIG. 1 shows the PLLA-degrading activity of the polyester degrading polypeptide of the invention. Active PLLA-degrading enzymes have been successfully recovered from *Micromonospora* strain of the invention "S0002" liquid culture supernatant. PLLA-degrading activity could be detected in enzymes recovered from minimal medium, R2 medium, and RS medium by using zymogram gels.

FIG. 2 shows the PLA degrading activity of a *Streptomyces lividans* host system expressing the polyester degrading polypeptide of the invention (culture supernatant) after 1 day and 6 days, compared to a control.

FIG. 3 is a sequence alignment of proteinase K (ProtK) (SEQ ID NO: 8), the Japanese enzyme as disclosed in Japanese patent JP2013000099 (SEQ ID NO: 9), and the polypeptide as set forth in SEQ ID No7 (also referred as polypeptide M2). According to protein sequences alignment, polypeptide M2 (SEQ ID NO: 10) shares 27% identity with proteinase K and 41% identity with the JP2013000099 enzyme. The sequence of the polypeptide M2 consisting of the auxiliary peptide is contained in the box.

FIG. 4 shows a tangential filtration system for recovering/concentrating secreted enzymes. PLLA-degrading activity assay for samples from each step of experiment (as indicated).

FIG. 5 illustrates the pH influence on the activity of the polyester degrading polypeptide of the invention. A PLLA-degrading activity test has been performed under various pH. Enzyme samples were loaded onto emulsified-PLLA agarose plates made with buffers of various pH and incubated at 37° C. for 48 hours.

FIG. 6 shows the temperature influence on the activity of the polyester degrading polypeptide of the invention. A PLLA-degrading activity turbidity test has been performed at 37° C. (FIG. 6A) and 60° C. (FIG. 6B) respectively. The degradation of emulsified PLLA caused the decrease of turbidity.

FIG. 7 shows the degradation of industrial solid materials (high molecular weight, semi-crystalline PLA films) and the corresponding lactic acid recovery. The percentages of film weight loss are indicated. (A) Photos of a film degraded by secreted enzymes of *Micromonospora* strain S0002 of the invention at 37° C. for 48 hours, and of a control. (B) Photos of a film degraded by *Micromonospora* strain S0002 culture at 37° C. for 30 days, and of a control. (C) Graph showing the total film weight loss and the lactic acid produced and detected in the culture supernatant of (B).

Figure 10:
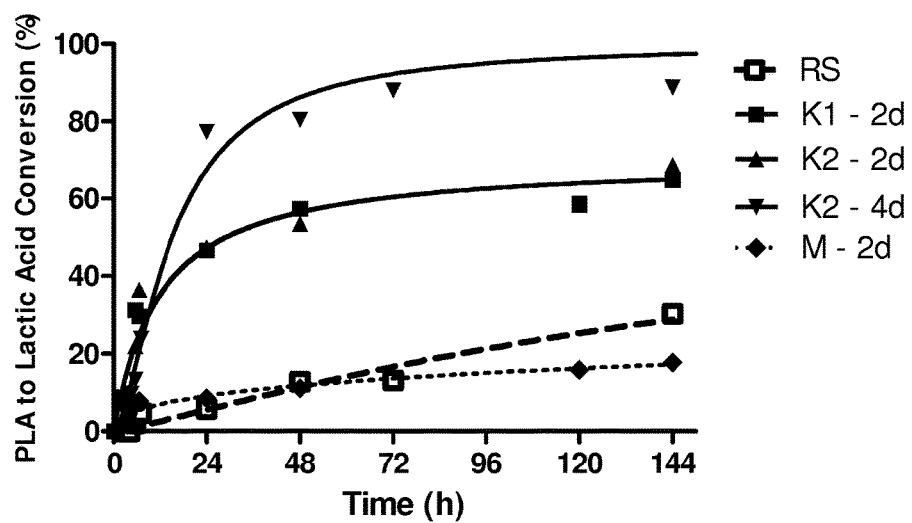

FIG. 10 shows the conversion of PLA into lactic acid at 37° C. and pH 10, using crude supernatants from *Micromonospora* strain S0002, preliminary grown under different conditions, i. e. after 20 days in RS medium (RS), 2 days in MMK medium supplemented (K1-2d and K2-2d) or not (M) with 10 g·L−1 (K1-2d) or 20 g·L−1 (K2-2d) gelatin and 4 days in MMK medium supplemented with 20 g·L−1 gelatin (K2-4d).

Figure 11:
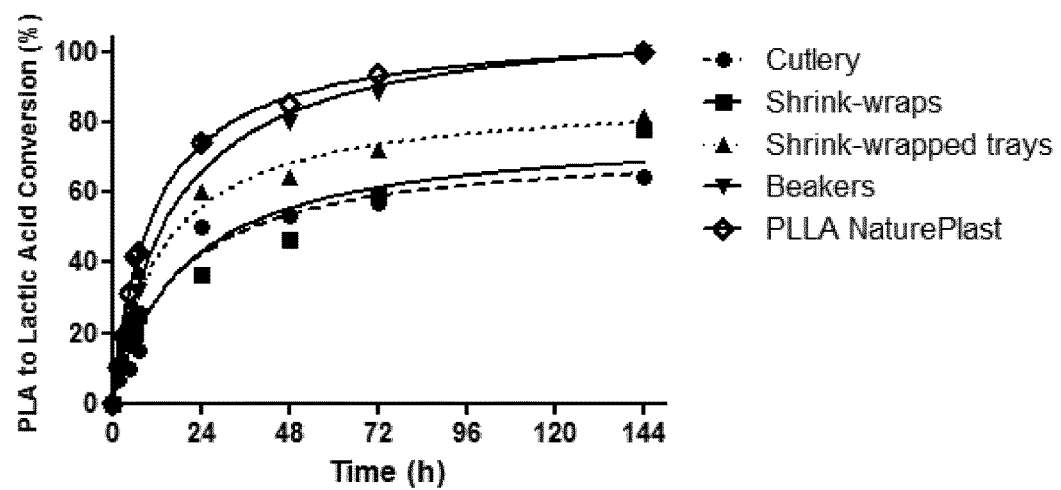

FIG. 11 illustrates the degradation of various commercial objects containing PLA by polypeptide M2 (percentage of conversion of PLA into lactic acid by time).

DETAILED DESCRIPTION OF THE INVENTION

The following is a description of the present invention, including preferred embodiments thereof given in general terms. The present invention is further exemplified in the disclosure given under the heading "Examples" herein below, which provides experimental data supporting the invention and means of performing the invention.

Definitions

The present disclosure will be best understood by reference to the following definitions.

The term "isolated" and "purified", in relation with a material, are used interchangeably and mean that said material (e.g., peptide, nucleic acid, cell) is removed from its original or natural environment. For instance, an isolated polypeptide is typically devoid of at least some polypeptides or other constituents of the cells to which it is normally associated or with which it is normally admixed or in solution. An isolated polypeptide includes said naturally-produced polypeptide in a purified or partially purified form, the recombinant polypeptide, the polypeptide which is expressed or secreted by a host cell, as well as the polypeptide in a host cell or culture or extract thereof. In relation to a nucleic acid, the term isolated indicates e.g., that the nucleic acid is not in its natural genomic context (e.g., in a vector, an expression cassette, linked to a promoter, or artificially introduced in a heterologous host cell). An isolated strain refers to a microbial cell that has been extracted from its natural or original environment.

As used herein, the term "strain" refers to microorganisms of a particular species which have common characteristics.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as see Worldwide Website: blast.ncbi.nlm.nih.gov/ or see Worldwide Website: ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The term "expression", as used herein, refers to any step involved in the production of a polypeptide including, but being not limited to, transcription, post-transcriptional modification, translation, post-translational modification, and secretion.

Herein, the terms "peptide", "polypeptide", "protein" and "enzyme" are employed interchangeably and refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the context of the invention, a "polyester containing material", also referred as "plastic product containing polyester" refers to a product, such as plastic product or plastic article, comprising at least one polyester in crystalline, semi-crystalline or totally amorphous forms. In a particular embodiment, the polyester containing material refers to any item made from at least one plastic material, such as plastic sheet, tube, rod, profile, shape, film, massive block etc., which contains at least one polyester, and possibly other substances or additives, such as plasticizers, mineral or organic fillers. In a particular embodiment, the polyester containing material contains polyester and at least one additional polymer, such as a polyolefin, arranged relative to each other in such a way that they cannot be easily separated. Preferably the polyester containing material is constituted of a mix of crystallized and amorphous polyesters, and/or semi-crystallized polyesters, and additives. More preferably, the polyester containing material is a manufactured product like packaging, agricultural films, disposable items or the like.

In the present description, "polyesters" encompass but is not limited to polyethylene terephthalate (PET), polytrimethylene terephthalate (PTT), polybutylen terephthalate (PBT), polyethylene isosorbide terephthalate (PEIT), polylactic acid (PLA), poly(L-lactic acid) (PLLA), poly(D-lactic acid) (PDLA), poly(D,L-lactic acid) (PDLLA), PLA stereocomplex (scPLA), polyhydroxyalkanoate (PHA), Poly(3-hydroxybutyrate) (P(3HB)/PHB), Poly(3-hydroxyvalerate) (P(3HV)/PHV), Poly(3-hydroxyhexanoate) (P(3HHx)), Poly(3-hydroxyoctanoate) (P(3HO)), Poly(3-hydroxydecanoate) (P(3HD)), Poly(3-hydroxybutyrate-co-3-hydroxyvalerate) (P(3HB-co-3 HV)/PHBV), Poly(3-hydroxybutyrate-co-3-hydroxyhexanoate) (P(3HB-co-3HHx)/(PHBHHx)), Poly(3-hydroxybutyric acid-co-4-hydroxybutyric acid) (P(3HB-co-4HB)), Poly(3-hydroxybutyrate-co-5-hydroxyvalerate) (PHB5HV), Poly (3-hydroxybutyrate-co-3-hydroxypropionate) (PHB3HP), Polyhydroxybutyrate-co-hydroxyoctonoate (PHBO), polyhydroxybutyrate-co-hydroxyoctadecanoate (PHBOd), Poly (3-hydroxybutyrate-co-3-hydroxyvalerate-co-4-hydroxybutyrate) (P(3HB-co-3HV-co-4HB)), polybutylene succinate (PBS), polybutylene succinate adipate (PBSA), polybutylene adipate terephthalate (PBAT), polyethylene furanoate (PEF), Polycaprolactone (PCL), poly(ethylene adipate) (PEA) and blends/mixtures of these polymers.

A "polymer" refers to a macromolecule whose structure is constituted of multiple repeating units linked by covalent chemical bonds. Within the context of the invention, the term polymer encompasses natural and synthetic polymers, constituted of a single type of monomer (i.e., homopolymers) or of two or more different types of monomers (i.e., copolymers).

According to the invention, "oligomers" refer to molecules containing from 2 to about 20 monomer units.

According to the invention, the expression "having polyester degrading activity", in relation with a polypeptide, composition or cell, refers to an ability to produce monomers and/or oligomers from polyesters and/or to diminish in weight a polyester containing material.

In the context of the invention, the "optimum temperature" of an enzyme refers to the temperature at which the rate of reaction of said enzyme is the highest, i.e. the temperature that the enzyme works optimally. Generally speaking, the increase of the temperature increases the rate of the reaction up to said optimum temperature. Beyond said optimum temperature, the enzyme loses its activity and is denaturized. Each enzyme has its own optimum temperature that can be easily determined by techniques known per se in the art. The activity range for an enzyme is thus determined by the temperature to which the activity starts and the temperature to which the protein starts to denature.

New Polypeptides

The present invention is directed to a new polypeptide having the ability to degrade plastics having ester bonds in their molecular structure. More particularly, the present invention discloses a newly identified and isolated polypeptide that exhibits a polyesterase activity. Said polypeptide was originally isolated from a natural *Micromonospora* strain. Interestingly, the polypeptide of the invention is capable of hydrolyzing ester bonds in natural and man-made polyesters. The invention also relates to an auxiliary polypeptide which has no degrading activity per se, that may be used with an enzyme to decrease its optimum temperature and/or to generally increasing the rate of reaction of said enzyme in the activity range.

It is therefore an object of the invention to provide a polypeptide having a polyester degrading activity and comprising at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity.

In the context of the invention, the expression "polypeptide having a polyester degrading activity", "polypeptide having a polyesterase activity" or "polyesterase" are used interchangeably to refer to same enzyme that is able to hydrolyze ester bonds.

According to the invention, the polypeptide has the ability to degrade polyesters up to monomers and oligomers. Interestingly, the polypeptide of the invention is able to degrade amorphous, crystallized and semi-crystallized polyesters. Furthermore, said polypeptide shows an unexpected degrading activity at low temperature (i.e., at about 30-40° C.), compared to polyesterases of the prior art.

In a particular embodiment, the polypeptide comprises all or a biologically active part of the amino acid sequence set forth in SEQ ID No1. A "biologically active part" of the polypeptide more specifically designates a portion of that polypeptide which confers or exhibits the polyesterase activity of the entire polypeptide. The active part may, for instance, confer substrate specificity or affinity, it may contain the catalytic site. An active part of the polypeptide also designates a mature form of the polypeptide (i.e., that does not contain a signal peptide at the N-terminal end of the polypeptide). In an embodiment, the biologically active part comprises the amino acids 125 to 376 of SEQ ID No1 that contain the catalytic sites and the calcium binding sites of the polypeptide. In another particular embodiment, the biologically active part comprises the amino acids 150-190, 245-275, and 335-345 of SEQ ID No1 that contain the catalytic triad and active sites of the polypeptide.

It is a further embodiment of the invention to provide a polypeptide comprising or consisting of the amino acid sequence set forth in SEQ ID No1.

In a particular embodiment, the polyester degrading polypeptide further comprises at least 75%, 80%, 85%, 90%, 95%, 99% or 100% identity to the full length amino acid sequence set forth in SEQ ID No3.

Preferably, the partial or full length amino acid sequence of SEQ ID No3 is located at the C-terminal end or N-terminal end of the partial or full length amino acid sequence of SEQ ID No1. This additional amino acid sequence forms an auxiliary polypeptide that allows to decrease the optimum temperature of the polyester degrading polypeptide of the invention. The auxiliary peptide may also increase the activity range of the polyester degrading polypeptide. In a preferred embodiment, the auxiliary polypeptide is fused to the polyester degrading polypeptide. However, said auxiliary polypeptide may also be used in mixture with the polyester degrading polypeptide. In a particular embodiment, the auxiliary polypeptide comprises at least amino acids 149 to 226 of SEQ ID No3.

It is therefore a further object of the invention to provide an auxiliary peptide comprising at least 75%, 80%, 85%, 90%, 95%, 99% or 100% identity to the full length amino acid sequence set forth in SEQ ID No3. Said auxiliary peptide may be fused to an enzyme, such as a depolymerase, and preferably to the C or N-terminal end of such enzyme. Alternatively, the auxiliary polypeptide may be used in mixture with an enzyme.

The enzymes of the invention are particularly active in a range of temperatures from about 20° C. to about 70° C., preferably from 30° C. to 55° C., more preferably from 30° C. to 40° C., even more preferably at 37° C. By use of the auxiliary polypeptide of the invention, the optimum temperature of the enzymes may be decreased up to 40° C., 39° C., 38° C., 37° C., 36° C., 35° C., or below. Similarly, by use of the auxiliary polypeptide the activity range of the enzymes of the invention may be increased from about 20° C. to about 70° C.

The polyester degrading polypeptides of the invention are particularly active in a range of pH from 5 to 11, preferably in a range of pH from 8 to 11, more preferably at pH 10.

The polyester degrading polypeptides of the invention advantageously have a productivity of at least 0.02 $g \cdot mg^{-1} \cdot h^{-1}$, 0.05 $g \cdot mg^{-1} \cdot h^{-1}$, 0.1 $g \cdot mg^{-1} \cdot h^{-1}$, 0.15 $g \cdot mg^{-1} \cdot h^{-1}$, 0.2 $g \cdot mg^{-1} \cdot h^{-1}$, 0.5 $g \cdot mg^{-1} \cdot h^{-1}$, 1 $g \cdot mg^{-1} \cdot h^{-1}$, 1.5 $g \cdot mg^{-1} \cdot h^{-1}$ or 2 $g \cdot mg^{-1} \cdot h^{-1}$. By "productivity" is meant the amount of product of degradation (i.e., monomers) formed per unit of polypeptide and per unit time, at a pH comprised between 9 and 11 and at a temperature of 37° C.+/−5° C.

The polypeptides of the invention are particularly useful for degrading polylactic acid (PLA), and more particularly poly(L-lactic acid) (PLLA) or poly(D-lactic acid) (PDLA). The polypeptides of the invention are also particularly useful for degrading polybutylene succinate (PBS) and polyhydroxyalkanoates (PHAs).

The invention further relates to a depolymerase comprising an auxiliary peptide having at least 75%, 80%, 85%, 90%, 95%, 99% or 100% identity to the full length amino acid sequence set forth in SEQ ID No3. In a particular embodiment, the auxiliary peptide is located at the N- or C-terminal end of the depolymerase. Advantageously, the depolymerase is a polyesterase.

Generally speaking, the use of the auxiliary polypeptide together with a depolymerase allows to decrease the optimum temperature of said depolymerase. The use of the auxiliary peptide with a depolymerase allows also to increase the activity range of said depolymerase.

In a particular embodiment, the polypeptides of the invention are immobilized on a solid support. The polypeptide may be immobilized by any appropriate method described in the state in the art, for instance, covalent binding, adsorption, entrapment or membrane confinement. A wide variety of supports may be used for immobilizing the polypeptide of the invention. The support to select depends on its dedicated use. Convenient supports encompass, without being limited to, plastic, metal, inorganic support such as glass, silica, alumina, bentonite, hydroxyapatite, nickel/nickel oxide, titanium, zirconia, polymeric supports and the like. The support may be in the form of a surface, a powder, micro- or nanobeads, a gel, a solvent-swelling or water-swelling gel or matrix, a reticulated matrix or gel, a membrane, a fibrous support, a porous support and the like. The methods for immobilizing the polypeptide are well-known to the skilled artisan (see for instance, Tischer and Wedekind, Topics in Current Chemistry, 1999, 200, 95-126 and Alloue et al, Biotechnol Agron Soc Environ 2008, 12, 57-68; the disclosure thereof being incorporated herein by reference).

Once prepared, the support of the invention can be directly used in a reaction medium. In other words, the support of the invention may be merely added in the reaction medium. When the support is solvent-swelling, the solvent of the reaction may be selected so as to provide an appropriate swelling of the support to render accessible the immobilized polypeptide without impairing the catalytic activity of the polypeptide. As an alternative, the support can be used to prepare a reactor, which can be for instance an enzyme reactor, a membrane reactor, a continuous flow reactor such as a stirred tank reactor, a continuously operated packed bed reactor, or a continuously operated fluidized bed reactor, or a packed bed reactor. In some embodiments, the support of the invention is recyclable and may be used several times in a row.

Nucleic Acids

A further object of the invention is a nucleic acid encoding a polypeptide as defined above.

As used herein, the term "nucleic acid", "nucleic sequence," "polynucleotide", "oligonucleotide" and "nucleotide sequence" are used interchangeably and refer to a sequence of deoxyribonucleotides and/or ribonucleotides. The nucleic acids can be DNA (cDNA or gDNA), RNA, or a mixture of the two. It can be in single stranded form or in duplex form or a mixture of the two. It can be of recombinant, artificial and/or synthetic origin and it can comprise modified nucleotides, comprising for example a modified bond, a modified purine or pyrimidine base, or a modified sugar.

The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding the polypeptide as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding the polypeptides of the invention, wherein the sequence of said nucleic acids, or a portion of said sequence at least, has been engineered using optimized codon usage.

A specific embodiment of this invention resides in an isolated nucleic acid encoding a polypeptide having a polyesterase activity, comprising the sequence set forth in SEQ ID No2.

A further embodiment of this invention resides in an isolated nucleic acid encoding a polypeptide having a polyesterase activity and further comprising the sequence set forth in SEQ ID No4.

A specific embodiment of this invention resides in an isolated nucleic acid encoding a polypeptide having a polyesterase activity, comprising the sequence set forth in SEQ ID No6.

Another specific embodiment of this invention resides in an isolated nucleic acid encoding a polyester degrading enzyme and further comprising the sequence set forth in SEQ ID No4.

Alternatively, the nucleic acids according to the invention may be deduced from the sequence of the polypeptides according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of this invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. Bacterial expression vectors well known in the art include pET11a (Novagen), lamda gt11 (Invitrogen).

The present invention further relates to the use of a nucleic acid, expression cassette or vector according to the invention to transform, transfect or transduce a host cell. The choice of the vector will typically depend on the compatibility of the vector with the host cell into which the vector is to be introduced.

The term "recombinant" refers to a nucleic acid construct, a vector, a polypeptide or a cell produced by genetic engineering.

The present invention also relates to a host cell, or recombinant cell, comprising a nucleic acid, cassette or vector according to the invention. The host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The expression cassette or vector may be introduced into host cells using standard techniques. Examples of such techniques include transformation, transfection, lipotransfection, protoplast fusion, and electroporation.

The host cell may be any cell that can be genetically modified and, preferably, cultivated. The cell can be eukaryotic or prokaryotic, such as a mammalian cell, an insect cell, a plant cell, a microorganism such as yeast, fungus or bacterial cell, etc. In a particular embodiment, the host cell is selected from the group of Bacillus, Lactic acid bacteria, Streptomyces, Trichoderma, Aspergillus, Pichia, Yarrowia or Micromonospora. It should be understood that the invention is not limited with respect to any particular cell type, and can be applied to all kinds of cells, following common general knowledge. The term "host cell" also encompasses any progeny of a parent host cell that is not identical to the parent host cell due to mutations that occur during replication.

In a particular embodiment, the present invention provides a host cell engineered to express the nucleic acids set forth in SEQ ID No2 or expression cassette thereof. In further particular embodiment, the present invention provides a host cell engineered to express the nucleic acids further comprising the sequence set forth in SEQ ID No4 or expression cassette thereof.

In another particular embodiment, the present invention provides a host cell engineered to express the nucleic acids set forth in SEQ ID No6 or expression cassette thereof.

In a further embodiment, the present invention provides a host cell comprising and expressing a nucleotide sequence encoding a polypeptide comprising at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity, and having a polyester degrading activity. In a further embodiment, the host cell comprises and expresses a nucleotide sequence encoding an auxiliary polypeptide comprising at least 75%, 80%, 85%, 90%, 95%, 99% or 100% identity to the full length amino acid sequence set forth in SEQ ID No3.

In a preferred embodiment, such host cell expresses a recombinant polypeptide containing both at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity, and at least 75%, 80%, 85%, 90%, 95%, 99% or 100% identity to the full length amino acid sequence set forth in SEQ ID No3. In a particular embodiment, the auxiliary polypeptide sequence is located at the C- or N-terminal end of the recombinant polypeptide. Alternatively, the host cell may express the polyesterase and the auxiliary polypeptide independently from each other.

In a particular embodiment, the present invention provides such a host cell having a polyester degrading activity, more preferably a PLA degrading activity, or a PBS degrading activity or a PHA degrading activity.

In a particular embodiment, the host cell is a recombinant microorganism, such as a fungus, a yeast or a bacterium. Preferably the recombinant microorganism is chosen among microorganisms having originally a polyester degrading activity.

Isolated *Micromonospora* Strain

It is a further object of the invention to provide an isolated bacterial strain of the genus *Micromonospora* expressing and optionally excreting a polypeptide as defined above.

In a particular embodiment, the isolated *Micromonospora* expresses a polypeptide having a polyester degrading activity and comprising at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity. In a further embodiment, the isolated *Micromonospora* strain expresses such a polypeptide further comprising at least 75%, 80%, 85%, 90%, 95%, 99% or 100% identity to the full length amino acid sequence set forth in SEQ ID No3, preferably located at the C-terminal end or at the N-terminal end of the polyester degrading polypeptide.

The invention further relates to a method for screening bacteria to select a *Micromonospora* expressing a polypeptide having a polyester degrading activity, comprising (a) Collecting and growing bacteria on PLA support;
(b) Isolating bacteria exhibiting a degradation halo on the PLA support; and
(c) Selecting from the isolated bacteria of step (b) a *Micromonospora* strain whose 16S rRNA gene sequence comprises at least 75%, 80%, 85%, 90%, 95%, 99% or 100% identity to the full length amino acid sequence set forth in SEQ ID No7.

In a particular embodiment, the method further comprises a step of selecting from the isolated *Micromonospora* of step c) a *Micromonospora* that expresses a polypeptide comprising at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity.

The invention further relates to an isolated *Micromonospora* strain whose 16S rRNA gene sequence comprises at least 75%, 80%, 85%, 90%, 95%, 99% or 100% identity to the full length amino acid sequence set forth in SEQ ID No7.

In a preferred embodiment, the isolated *Micromonospora* strain is active in a range of temperatures from 20° C. to 70° C., preferably from 30° C. to 55° C., more preferably from 30° C. to 40° C., even more preferably at 37° C.

Advantageously, the isolated *Micromonospora* strain is active in a range of pH from 5 to 11, preferably in a range of pH from 8 to 11, more preferably at pH10.

In a preferred embodiment, the isolated *Micromonospora* strain has a polylactic acid (PLA) degrading activity, and more particularly a poly(L-lactic acid) (PLLA) or a poly(D-lactic acid) (PDLA) degrading activity. In another preferred embodiments, the isolated *Micromonospora* strain has a polybutylene succinate (PBS) degrading activity and/or a polyhydroxyalkanoates (PHAs) degrading activity.

Method for Producing the Polyester Degrading Polypeptide

It is a further object of the invention to provide a method of producing a polyester degrading polypeptide as defined above, comprising (i) culturing a recombinant cell or a *Micromonospora* as defined above, (ii) recovering the culture supernatant, and optionally (iii) isolating or purifying the polypeptide. The invention further relates to such polypeptide obtained by this method of production.

The polypeptides of the invention may be produced by recombinant techniques, or it may be isolated or purified from natural sources and more particularly from *Micromonospora* strains, or it may be artificially produced. Within the context of the invention, the term "derived from a microorganism" in relation to a polypeptide indicates that the polypeptide has been isolated from such a microorganism, or that the polypeptide comprises all or a biologically active part of the amino acid sequence of a polypeptide isolated or characterized from such a microorganism. Alternatively, the polypeptide of the invention may be produced via cell free methods (Kim et al. J Biosci. Bioeng. July 2009; Spirin et al. (2007) Front Matter in Cell-Free Protein Synthesis: Methods and Protocols) or may be chemically synthesized.

The polypeptide of the invention may be purified by techniques known per se in the art, such as chromatography (e.g. ion exchange, affinity, size-exclusion, reversed-phase, etc.) and precipitation (e.g. salt-out, isoelectric point, organic solvents, non-ionic hydrophilic polymers, etc.) and stored under conventional techniques. The polypeptide may be further modified to improve e.g., its stability or activity. It may be used as such, in purified form, either alone or in combinations with additional enzymes, to catalyze enzymatic reactions involved in the degradation and/or recycling of a polyester containing material. The polypeptide may be in soluble form, or on solid phase. In particular, it may be bound to cell membranes or lipid vesicles, or to synthetic supports such as glass, plastic, polymers, filter, membranes, e.g., in the form of beads, columns, plates and the like.

Polyester Degrading Compositions

It is a further object of the invention to provide a composition comprising a polypeptide having a degrading activity, recombinant cell(s), isolated *Micromonospora* strain, or extract thereof, as defined above, and optionally additives, excipients and/or reagents etc. Appropriate excipients encompass buffers commonly used in biochemistry, agents for adjusting pH, preservatives such as sodium benzoate, sodium sorbate or sodium ascorbate, conservatives, protective or stabilizing agents such as starch, dextrin, arabic gum, salts, sugars e.g. sorbitol, trehalose or lactose, glycerol, polyethyleneglycol, polyethene glycol, polypropylene glycol, propylene glycol, sequestering agent such as EDTA, amino acids, a carrier such as a solvent or an aqueous solution, and the like.

In the context of the invention, the term "composition" encompasses all kind of compositions comprising the polypeptide of the invention. The composition may be in solid or liquid state, such as a solution, suspension, paste, gel, lyophilisate, powder or frozen preparation. In a preferred embodiment, the composition is a lyophilisate.

The composition of the invention may be obtained by mixing the polypeptide with one or several excipients. The composition of the invention may comprise from 0.1% to 90%, preferably from 0.1% to 50%, more preferably from 0.1% to 30%, even more preferably from 0.1% to 5% by weight of the polypeptide of the invention and from 10% to 99.9%, preferably from 50% to 99.9%, more preferably from 30% to 99.9%, even more preferably from 95% to 99.9% by weight of excipient(s). A preferred composition comprises between 0.1 and 5% by weight of the polypeptide of the invention.

In a particular embodiment, the composition comprises at least a polyesterase having at least 75%, 80%, 85%, 90%, 95%, 99% or 100% identity to the full length amino acid sequence set forth in SEQ ID No1, preferably at least 90%, 91%, 92%, 93%, 94%, 95%, 96%, 97%, 98%, 99% or 100% identity. Advantageously, the composition further comprises an auxiliary peptide having at least 75%, 80%, 85%, 90%, 95%, 99% or 100% identity to the full length amino acid sequence set forth in SEQ ID No3. Preferably, the auxiliary peptide is fused to the C- or N-terminal end of the polyesterase. Alternatively, the polyesterase and the auxiliary peptide are in admixture in the composition.

The invention further provides a the composition comprising a depolymerase, preferably a polyesterase, comprising at the C- or N-terminal end an auxiliary peptide having at least 75%, 80%, 85%, 90%, 95%, 99% or 100% identity to the full length amino acid sequence set forth in SEQ ID No3.

According to the invention, the composition may further comprise additional polypeptide(s) exhibiting an enzymatic activity. The amounts of polypeptide of the invention will be easily adapted by those skilled in the art depending e.g., on the nature of the polyester containing material to degrade and/or the additional enzymes/polypeptides contained in the composition.

In a particular embodiment, the polypeptide of the invention is solubilized in an aqueous medium together with one or several excipients, especially excipients which are able to stabilize or protect the polypeptide from degradation. The resulting mixture may then be dried, lyophilized or atomized so as to obtain a powder.

In a further particular embodiment, the composition of the invention comprises at least one recombinant cell expressing the polypeptide of the invention, or an extract thereof. An "extract of a cell" designates any fraction obtained from a cell, such as a cell supernatant, cell debris, cell walls, DNA extract, enzymes or enzyme preparation or any preparation derived from cells by chemical, physical and/or enzymatic treatment, which is essentially free of living cells. Preferred extracts are enzymatically-active extracts. The composition of the invention may comprise one or several recombinant cells of the invention or extract thereof, and optionally one or several additional cells. Alternatively, or in addition, the composition may comprise a wild type *Micromonospora* as defined above, expressing the polypeptide of the invention, or an extract thereof. Preferred extracts are enzymatically-active extracts.

In a particular embodiment, the composition consists or comprises a lyophilized culture medium of a recombinant microorganism expressing and excreting the polypeptide of the invention and/or a *Micromonospora* of the invention expressing. In a particular embodiment, the powder comprises the polypeptide of the invention and a stabilizing/solubilizing amount of sorbitol or dextrin, such as maltodextrine and/or cyclodextrine.

In a further embodiment, the polypeptide of the invention is immobilized on a solid support. The polypeptide may be immobilized by any appropriate method described in the state in the art, for instance, covalent binding, adsorption, entrapment or membrane confinement. A wide variety of supports may be used for immobilizing the polypeptide of the invention. The support to select depends on its dedicated use. Convenient supports encompass, without being limited to, plastic, metal, inorganic support such as glass, silica, alumina, bentonite, hydroxyapatite, nickel/nickel oxide, titanium, zirconia, polymeric supports and the like. The support may be in the form of a surface, a powder, micro- or nanobeads, a gel, a solvent-swelling or water-swelling gel or matrix, a reticulated matrix or gel, a membrane, a fibrous support, a porous support and the like. The methods for immobilizing the polypeptide are well-known to the skilled artisan (see for instance, Tischer and Wedekind, Topics in Current Chemistry, 1999, 200, 95-126 and Alloue et al, Biotechnol Agron Soc Environ 2008, 12, 57-68; the disclosure thereof being incorporated herein by reference).

Once prepared, the support of the invention can be directly used in a reaction medium. In other words, the support of the invention may be merely added in the reaction medium. When the support is solvent-swelling, the solvent of the reaction may be selected so as to provide an appropriate swelling of the support to render accessible the immobilized polypeptide without impairing the catalytic activity of the polypeptide. As an alternative, the support can be used to prepare a reactor, which can be for instance an enzyme reactor, a membrane reactor, a continuous flow reactor such as a stirred tank reactor, a continuously operated packed bed reactor, or a continuously operated fluidized bed reactor, or a packed bed reactor. In some embodiments, the support of the invention is recyclable and may be used several times in a row.

Methods for Degrading a Polyester Containing Material

The present invention provides methods using the polypeptide(s) of the invention for degradation and/or recycling of polyester containing material, as plastic products made or containing polyesters. Indeed, due to its high polyester depolymerizing efficiency, the polyesterase of the invention is much more advantageous in comparison with other known chemical or microbial polyester degradation means. The polypeptide of the invention may be particularly useful for degrading with an interesting rate PLA, PBS and/or PHAs containing material.

It is therefore an object of the invention to use a polyester degrading polypeptide of the invention, or corresponding recombinant cell or extract thereof, or isolated *Micromonospora* strain, or composition for the enzymatic degradation of a polyester containing material. In a particular embodiment, the polypeptide, or corresponding recombinant cell, extract thereof, or isolated *Micromonospora* strain, or composition is used for the enzymatic degradation of a PLA containing material, and more preferably for the enzymatic degradation of a PLLA or PDLA containing material. In another particular embodiment, the polypeptide, or corresponding recombinant cell, extract thereof, or isolated *Micromonospora* strain, or composition is used for the enzymatic degradation of a PBS containing material or PHAs containing material.

It is a further object of the invention to use an auxiliary peptide as defined above together with a depolymerase for degrading PLA, PBS and/or PHAs containing material. Advantageously, the auxiliary peptide is fused to the depolymerase, preferably to the C- or N-terminal end of the depolymerase.

It is another object of the invention to provide a method for degrading a polyester containing material, wherein a polyester containing material is contacted with the polypeptide of the invention, or corresponding recombinant cell or isolated *Micromonospora* strain, or extract thereof, or composition.

Advantageously, polyester(s) of the polyester containing material is(are) depolymerized up to monomers and/or oligomers. In a particular embodiment, all the targeted polyesters are depolymerized up to the monomers that formed the original polyesters of the material.

In an embodiment of the degradation process, at least one polyester is degraded to yield repolymerizable monomers and/or oligomers, which are advantageously retrieved in order to be reused.

In another embodiment, polyester(s) of the polyester containing material is(are) fully degraded.

In a particular embodiment, the polyester containing material comprises PLA, more preferably PLLA and/or PDLA, and at least lactic acid monomers and/or oligomers are recovered.

In a particular embodiment, the polyester containing material comprises PBS, and at least butanediol monomers and/or oligomers and/or succinic acid monomers and/or oligomers are recovered.

In a particular embodiment, the polyester containing material comprises PHA, more preferably (P(3HB-co-4HB), and at least hydroxyacids or hydroxybutyric acids monomers and/or oligomers are recovered.

In a further embodiment, the polyester containing material comprises PLA and at least one additional polyester, preferably selected from polytrimethylene terephthalate (PTT), polybutylene terephthalate (PBT), polyethylene terephthalate (PET), polybutylene adipate terephthalate (PBAT), polyhydroxyalkanoate (PHA), polybutylene succinate (PBS), polybutylene succinate-co-adipate (PBSA), polycaprolactone (PCL), poly(ethylene adipate) (PEA), and blends/mixtures of these polyesters.

In a particular embodiment, the polyester containing material comprises PBS and at least one additional polyester, preferably selected from polylactic acid (PLA), polytrimethylene terephthalate (PTT), polybutylene terephthalate (PBT), polyethylene terephthalate (PET), polybutylene adipate terephthalate (PBAT), polybutylene succinate-co-adipate (PBSA), polyhydroxyalkanoate (PHA), polycaprolactone (PCL), poly(ethylene adipate) (PEA), and blends/mixtures of these polyesters.

In a particular embodiment, the polyester containing material comprises PHA and at least one additional polyester, preferably selected from polylactic acid (PLA), polytrimethylene terephthalate (PTT), polybutylene terephthalate (PBT), polyethylene terephthalate (PET), polybutylene adipate terephthalate (PBAT), polybutylene succinate (PBS), polybutylene succinate-co-adipate (PBSA), polycaprolactone (PCL), poly(ethylene adipate) (PEA), and blends/mixtures of these polyesters.

Alternatively or in addition, the polyester containing material may further contain at least one polyamide (also called nylon) and/or at least one polyolefin, preferably selected from the group consisting of polyethylene (PE), polypropylene (PP), and blends/mixtures of these polyesters, and/or at least one vinyl polymer made from vinyl monomers, small molecules containing carbon-carbon double bonds.

According to the invention, the polyester containing material may also contain metal compounds, mineral compounds, glass compounds, natural or synthetic fibers, paper, wood, wood compounds as lignin, cellulose or hemi-cellulose, starch, and derivatives thereof.

The invention also relates to a method of producing monomers and/or oligomers from a polyester containing material, comprising exposing a polyester containing material to the polypeptide of the invention, or corresponding recombinant cell or isolated *Micromonospora* strain or extract thereof, or composition, and optionally recovering monomers and/or oligomers. The method of the invention is particularly useful for producing lactic acid monomers or butanediol monomers or succinic acid monomers or hydroxyl acids monomers.

When a recombinant microorganism is used, such microorganism advantageously exhibits a modified metabolism in order to prevent the consumption of the monomers and/or oligomers obtained from the degraded polyester. For example, the enzymes degrading said monomers and/or oligomers have been deleted or knocked out in the microorganism. Alternatively, the method of the invention may be performed in a culture medium containing at least one carbon source usable by the recombinant microorganism so that said microorganism preferentially consumes this carbon source instead of the monomers and/or oligomers. Advantageously, the polyester containing material is contacted with a culture medium containing the recombinant microorganisms, glucose or the like as a carbon source, as well as an available nitrogen source, including an organic nitrogen source (e.g., peptone, meat extract, yeast extract, corn steep liquor) or an inorganic nitrogen source (e.g., ammonium sulfate, ammonium chloride). If necessary, the culture medium may further contain inorganic salts (e.g., sodium ion, potassium ion, calcium ion, magnesium ion, sulfate ion, chlorine ion, phosphate ion). Moreover, the medium may also be supplemented with trace components such as vitamins, oligo-elements and amino acids.

In a particular embodiment, the polyester containing material may be pretreated prior to be contacted with the polyesterase of the invention, in order to physically change its structure, so as to increase the surface of contact between the polyesters and the polyesterase. For example, the polyester containing material may be transformed to an emulsion or a powder, which is added to a liquid medium containing the polypeptide of the invention and/or recombinant microorganism or extract thereof. Alternatively, the polyester containing material may be mechanically ground, granulated, pelleted, etc. by cutting, impact, crushing, grinding, fractionation, cryogenic grinding, or the like, to reduce the shape and size of the material prior to be added to a liquid medium containing the recombinant microorganism, extract thereof and/or polypeptide. The mechanical pretreatment can also be a sonication, a centrifugation, a shear, a collisop, a high-pressure homogenizer, a maceration or a liquefaction with a rotary drum, a screw press, a disc screen shredder, or a piston press. Alternatively or additionally, a thermal pretreatment can be applied. It can be achieved with microwaves. Such thermal pretreatment may provide disinfection, pasteurization or sterilization. In another embodiment, the polyester containing material is chemically pretreated to modify its structure and increase the surface of contact between the polyesters and the polypeptide of the invention. A base, an acid, a solvent or an ionic liquid can be used. An ozonation can also be implemented. A laser treatment can also be used. In a particular embodiment, the polyester containing material may also be sorted, washed, disinfected, sterilized and/or biologically cleaned prior to degradation. According to the invention, several pre-treatments may be combined.

The time required for degradation of a polyester containing material may vary depending on the polyester containing material itself (i.e., nature and origin of the plastic product, its composition, shape etc.), the type and amount of polypeptide used, as well as various process parameters (i.e., temperature, pH, additional agents, etc.). One skilled in the art may easily adapt the process parameters to the polyester containing material.

Advantageously, the process is implemented at a temperature comprised between 20° C. and 70° C., preferably between 30° C. and 55° C., more preferably from 30° C. to 40° C., even more preferably at about 37° C. More generally, the temperature is maintained below an inactivating temperature, which corresponds to the temperature at which the polypeptide is inactivated and/or the recombinant microorganism does no more synthesize the polypeptide. More generally, the temperature is maintained at the optimum temperature of the polypeptide of the invention. More particularly, this optimum temperature is lower when the polypeptide of the invention further comprises partially or full length sequence of the auxiliary polypeptide of the invention.

The pH of the medium may be in a range of pH from 5-11, preferably in a range of pH from 8-11, more preferably at pH 10. Advantageously, the pH is adjusted according to the targeted polyester and the solubility of the targeted monomers/oligomers for improving the process efficiency. Preferably, the pH is adjusted to be maintained at the optimum pH of the polypeptide. Indeed, depolymerization of polyesters produces acidic monomers and oligomers that induce a pH decrease. An addition of a diluted alkali can be used to compensate this acidification and maintain the pH to the optimum one.

Advantageously, the added amount of polypeptide is in a range of 0.001% to 5% by weight of polyester containing material, preferably in a range of 0.001% to 1%, more preferably in a range of 0.001% to 0.1%, even more preferably in a range of 0.001% to 0.05%.

In a particular embodiment, the process is performed under agitation, preferably comprised between 30 rpm and 2000 rpm, in order to favor contact between the polypeptide and the polyester containing material.

In a particular embodiment, at least a lipophilic agent and/or hydrophilic agent is added to the medium for improving the depolymerization step. An inductor such as oligomers of polyesters or derivatives thereof can be added to the medium comprising recombinant microorganism to improve polypeptide production. A surfactant such as Tween can be added to the medium to modify interface energy between the polyester and the polypeptide or recombinant microorganism and improve degradation efficiency. An organic substance or an ionic liquid could be used to swell the polyester and increase its accessibility to the microorganism or polypeptide.

The reaction time for depolymerization of at least one polyester of the polyester containing material up to monomers/oligomers is advantageously comprised between 5 and 110 hours, more preferably between 24 and 72 hours. More preferably, at least 50% of the polyester is depolymerized up to monomers/oligomers after 24 hours, even more preferably at least 80% of the polyester is depolymerized after 24 hours. Such reaction time may allow the depolymerization to advance sufficiently, and will not be economically detrimental. The reaction time can be longer for biodegradation.

Optionally, monomers and/or oligomers resulting from the depolymerization may be recovered, sequentially or continuously. A single type of monomers and/or oligomers or several different types of monomers and/or oligomers may be recovered, depending on the starting polyester containing material.

The recovered monomers and/or oligomers may be further purified, using all suitable purifying method and conditioned in a re-polymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not.

The repolymerizable monomers and/or oligomers may then be reused to synthesize polyesters. Advantageously, polyesters of same nature are repolymerized. However, it is possible to mix the recovered monomers and/or oligomers with other monomers and/or oligomers, in order to synthesize new copolymers.

In a particular embodiment, repolymerization is conducted using a hydrolase in appropriate conditions for allowing polymerization reaction. Initiators may be added to the monomers/oligomers solution to favour the polymerization reaction. One skilled in the art may easily adapt the process parameters to the monomers/oligomers and the polymers to synthesize.

In a particular embodiment, the methods of the invention are performed in a reactor. "Reactor" designates any device or installation or facility suitable for maintaining and transforming plastic articles. A reactor may comprise inlet and outlet devices to supply/collect medium, nutrients, gas, etc. The reactor may be closed or open, such as a tank.

Plastic Compound

It is a further object of the invention to provide a plastic compound containing the polypeptide of the invention and/or a recombinant microorganism and/or an isolated *Micromonospora* expressing and excreting said polypeptide or extract thereof; and at least one polyester. In a particular embodiment, the polyester is preferably poly(L-lactic acid) (PLLA) or poly(D-lactic acid) (PDLA), polybutylene succinate (PBS) degrading activity, or polyhydroxyalkanoates (PHAs). In some embodiments, the plastic compound may contain additional polymer(s), preferably selected from polyesters such as PBAT, PCL, PET; polyolefins such as polyethylene, polypropylene; or natural polymers such as starch, cellulose or flour; and blends/mixtures thereof. In a particular embodiment, the plastic compound contains in addition to the polyester mainly targeted by the polypeptide, at least one additional polymer selected from PBAT, flour and starch.

In a particular embodiment, the polypeptide used for preparing the plastic compound comprises an amino acid sequence having at least 75%, 80%, 85%, 90%, 92%, 95%, 99% or 100% identity to the full length amino acid sequence set forth in SEQ ID No1, preferably at least 90%, 91%, 92%, 93%, 94%, 95%, 96%, 97%, 98%, 99% or 100% identity.

In particular, the invention relates to a process for producing such plastic compound comprising a step of mixing a polyester and the polypeptide of the invention and/or microorganism of the invention and/or the recombinant cell of the invention or extract thereof that degrades said polyester, at a temperature at which the polyester is in a partially or totally molten state so that the polypeptides/microorganisms are integrated into the very structure of the polyester containing material. In a particular embodiment, the process is an extrusion process. In a particular embodiment, spores of the *Micromonospora* or of the recombinant microorganism are included into the plastic compound.

In some embodiments, the polypeptide and/or the recombinant microorganism of the invention and the polyester are mixed at a temperature between the glass transition temperature and the melting point of the polyester. Alternatively, the polypeptide/microorganism and the polyester are mixed at a temperature corresponding to the melting point of said polyester, or above. In a particular embodiment, the polypeptide/microorganism and polyester are mixed at a temperature between 80° C. and 250° C., preferably between 100° C. and 200° C. Alternatively, the polypeptide/microorganism and polyester are mixed at a temperature above 80° C., preferably, above 100° C., even more preferably above 130° C.

In some embodiments, the mixing step is performed using extrusion, twin screw extrusion, single screw extrusion, injection-molding, casting, thermoforming, rotary molding, compression, calendering, ironing, coating, stratification, expansion, pultrusion, extrusion blow-molding, extrusion-swelling, compression-granulation, water-in-oil-in-water double emulsion evaporation or any techniques known by person skilled in the art.

The resulting plastic compound integrates polypeptide/microorganism of the invention embedded in the mass of the compound.

Advantageously, such plastic compound can be used for the production of polyester containing materials and/or plastic article that will thus include the polypeptide of the invention.

In a particular embodiment, the plastic compound and the resulting plastic article are biodegradable. That means that they comply with at least one of the relevant standards and/or labels known by the person skilled in the art, such as standard EN 13432, standard ASTM D6400, OK Biodegradation Soil (Label Vinçotte), OK Biodegradation Water (Label Vinçotte), OK Compost (Label Vinçotte), OK Compost Home (Label Vinçotte).

Advantageously, a biodegradable plastic compound or biodegradable plastic article refers to a plastic compound or plastic article that is at least partially transformed under environmental conditions into water, carbon dioxide or methane and biomass. Preferred plastic compounds or plastic articles of the invention are biodegradable in water. Preferably, about 90% by weight of the plastic compound or plastic article is biodegraded in water within less than 90 days, more preferably within less than 60 days, even more preferably within less than 30 days. Alternatively or in addition, the plastic compound or plastic article may be biodegraded when exposed to wet and temperature conditions that occur in landscape. Preferably, about 90% by weight of the plastic compound or plastic article is biodegraded with less than 3 years in the environment, more preferably within less than 2 years, even more preferably within less than 1 year. Alternatively, the plastic compound or plastic article may be biodegraded under industrial composting conditions, wherein the temperature is maintained above 50° C.

Further aspects and advantages of the invention will be disclosed in the following examples, which should be considered as illustrative and do not limit the scope of this application.

EXAMPLES

Example 1. Identification of a *Micromonospora* Strain "S0002" and Secreted Enzymes Having a Polylactic Acid Degrading Activity A—S0002 *Micromonospora* Strain Isolation A strain with the ability to degrade PLA was isolated from a garden compost.

A number of PLA flower pots (Soparco, Condé-sur-Huisne, France) were buried in a household garden compost (around 50 cm from the surface). Every 3 months, one piece of PLA pot was removed from the compost for strain isolation (until 12 months). The PLA pot was cut into smaller pieces and then transferred into a 50 ml falcon tube containing 25 ml compost extract. After vigorously vortexing, suspension was plated after serial dilutions on compost extract agar plates containing 1 g/L emulsified PLA. After 15-30 days, translucent "clear-zone" surrounding the colony appeared reflecting the PLA degradation by the micro-organisms. These micro-organisms were selected for further confirmation.

The compost extract (CE) was prepared as follow: 100 g of compost was added into 800 mL $dH_2O$ and stirred for overnight. This mixture was then centrifuged at 5,000 rpm for 1 hour. The supernatant was filtered with 2 layers of filter paper, and the filtrate was then filled with $dH_2O$ to 1 liter. For the compost extract medium, polymers (1 g/L) were dissolved in organic solvent (dichloromethane or chloroform), added into the compost extract, and emulsified with a dispersion unit Ultra-Turrax®T 18 basic (IKA-Werke GmbH & Co. KG, Staufen, Germany). For plates, 1.5% agar was added before autoclaving.

Among all isolates, one strain, referred as S0002, exhibited distinguishable "clear-zone" on PLA agar plates. Based on the basic local alignment search tool (BLAST) result of searching and comparing 16S rRNA sequences in the GenBank database (see Worldwide Website: blast.ncbi.nlm.nih.gov/Blast.cgi), this strain was identified as taxonomically belonging to the genus of *Micromonospora*. This *Micromonospora* strain S0002 has a 16S rRNA consisting in SEQ ID No7.

The "clear-zone" phenomenon on agar plates indicated that the *Micromonospora* S0002 strain of the invention not only produces polymer-degrading enzymes, but also secretes them outside the cell.

These secreted enzymes were recovered and concentrated.

B—Enzymes Extraction

Figure 1:
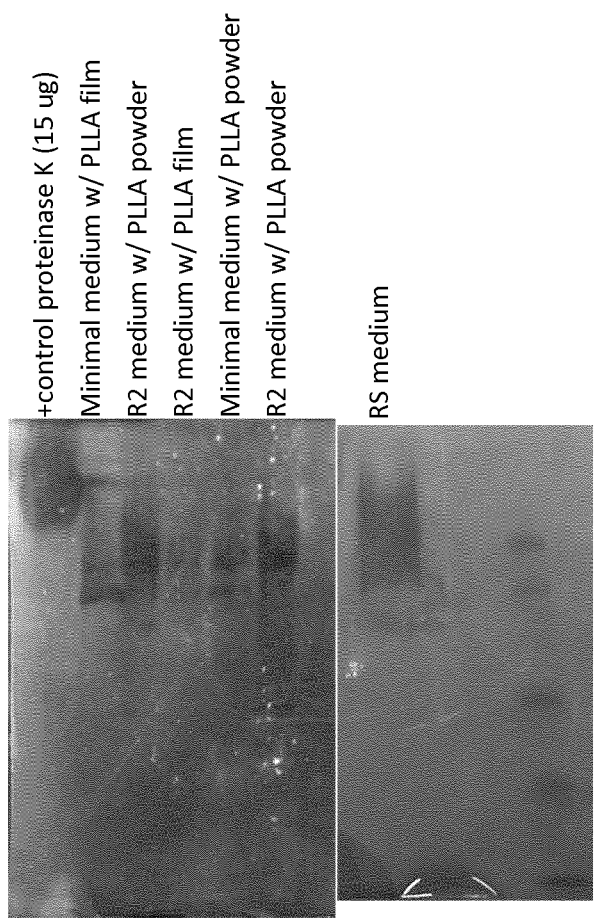

The extraction of secreted proteins from liquid culture supernatant was performed as follow: strain S0002 was grown in a medium at 37° C., 250 rpm shaking for 13 days. Secreted proteins of S0002 were collected from the culture supernatant using ammonium sulfate precipitation (80%). Pellets were dissolved in 50 mM Tris-HCl and then loaded into Amicon Ultra-10K filters (Millipore, Billerica, Mass., USA) for buffer exchange and volume reduction/concentration. The extraction was performed using 3 liquid media: minimal medium (with PLLA as the sole carbon source), R2 medium (a low nutrient medium supporting slow-growth bacteria), and RS medium (a rich medium). PLA-degrading activity could be detected in enzymes recovered from all 3 media (as showed on zymogram gels in FIG. 1). This result implies that, PLA-degrading enzymes are constitutively expressed by strain S0002, or at least, no special induction is needed.

Zymogram gel assay: PLA (emulsified in 0.1 M Tris pH 8) was added to 12% polyacrylamide resolving gel to 0.1% final concentration. Gels were casted and run as regular PAGE gels. After the electrophoresis finished, the gel was rinsed four times with milliQ water and then incubated in 50 mM Tris pH 8 and 2.5 mM $CaCl_2$ at 37° C. until clear bands appear.

C—Identification of a Polyesterase of the Invention M2, Produced from *Micromonospora* Strain S0002 of the Invention In order to identify enzymes that exhibit a PLA-degradation activity, both the genomics and the proteomics approaches were applied. Position of activated enzymes (clear-bands) on the zymogram gel was compared to supernatant proteins profile on Coomassie coloured gel. Bands from the coloured gel corresponding to active ones on zymogram were excised and subjected to liquid chromatography-tandem mass spectrometry (LC-MS-MS) analyses (Functional proteomic core facility, Institut de Physiologie et de Biologie Cellulaires, Universite de Poitiers, Poitiers, France). The Mascot software (Matrix Science Inc., Boston, Mass., USA) was used to interpret LC-MS-MS data and identify protein candidates from the translated S0002 genome (sequenced at the DNA sequencing platform, Laboratoire Ecologie et Biologie des Interactions, Université de Poitiers, Poitiers, France).

Figure 2:
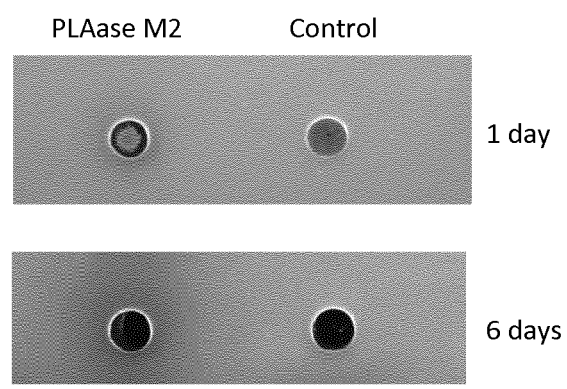

Candidate genes were amplified out of genomic DNA and sequences were proofread by using the Sanger analysis. Confirmed candidate genes were then cloned for heterologous expression, in the *Streptomyces lividans* host system. Transformation of *Streptomyces lividans* was performed according to established protocols [Nybo S E et al., 2010] [Kieser T, 2000]. Among those candidates that were expressed in *Streptomyces lividans*, one construct (contig 170-ORF5) has demonstrated PLA-degrading ability on R2-PLA plates (FIG. 2). According to the BLAST search result, contig 170-ORF5 is a homologue of probable peptidase S8/subtilisin-like serine proteases. Thus, from this result, contig 170-ORF5 in S0002 was identified that can degrade PLA. The corresponding enzyme has been called polypeptide M2 (or polyesterase M2).

The DNA sequence of polyesterase M2 is 1,866 bp (SEQ ID No6) which can be translated into a 621-amino acid sequence (SEQ ID No5). According to the result of conserved domain annotation (see Worldwide Website: ncbi.nlm.nih.gov/Structure/cdd/wrpsb.cgi), amino acid residue 1-26 contains a putative signal peptide, residue 27-116 contains a putative peptidase inhibitor domain, residue 117-376 contains a putative peptidase domain, and residue 377-621 contains a putative P-proprotein and FilD_N domains. Active sites (catalytic triad) of polyesterase M2 have been predicted within residue 150-190, residue 245-275, and residue 335-345. Calcium binding sites have been predicted within residue 125-135 and residue 290-315.

According to protein sequences alignment, polyesterase M2 shares 27% identities with proteinase K and 41% identities with a PLA degrading enzyme disclosed in the document JP2013000099. Polyesterase M2 is about 220 amino acids longer at the C-terminal as compared with the other two enzymes and blast searching conserved domains of this 226 amino acid sequence (SEQ ID No3) revealed a signature of "proprotein convertase P-domain" and is called the auxiliary polypeptide of the invention. Without considering the auxiliary polypeptide, polyesterase M2 shares 40% identities with proteinase K and 63% identities with the JP2013000099 enzyme (FIG. 3).

D—Secreted Enzymes Size Estimation

Figure 4:
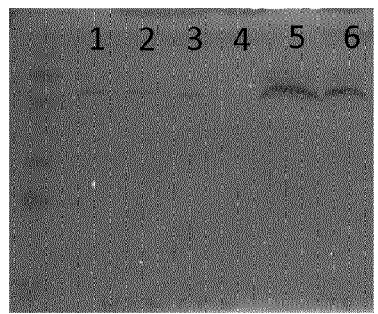

A larger volume of S0002 culture (500 mL) was grown and tested with the tangential flow filtration system (Sartorius AG, Goettingen, Germany). The tangential flow filtration system is widely used in industry for large scale recovering and concentrating secreted biological products. The S0002 culture first flew through 0.2 µm membranes in order to exclude bacteria cells. The cell-free culture liquid then cross-flew the filter unit containing membrane with cut-off size 30 kDa, and the final volume of concentrated sample was 14 ml. During the whole process, samples were reserved in each step of experiment for PLLA-degradation activity assay. As shown in the zymogram gel (FIG. 4), PLA-degradation activity was detected in the S0002 culture before 0.2 µm membrane filtration, after 0.2 µm membrane filtration, and after 30 kDa cut-off membrane concentrated fraction. Only the fraction of <30 kDa filtrate had no activity. This suggests active enzyme(s) is/are larger than 30 kDa in size.

Example 2. Characterization of PLA Depolymerase(s) from *Micromonospora* Strain S0002 Including Polyesterase M2

Figure 5:
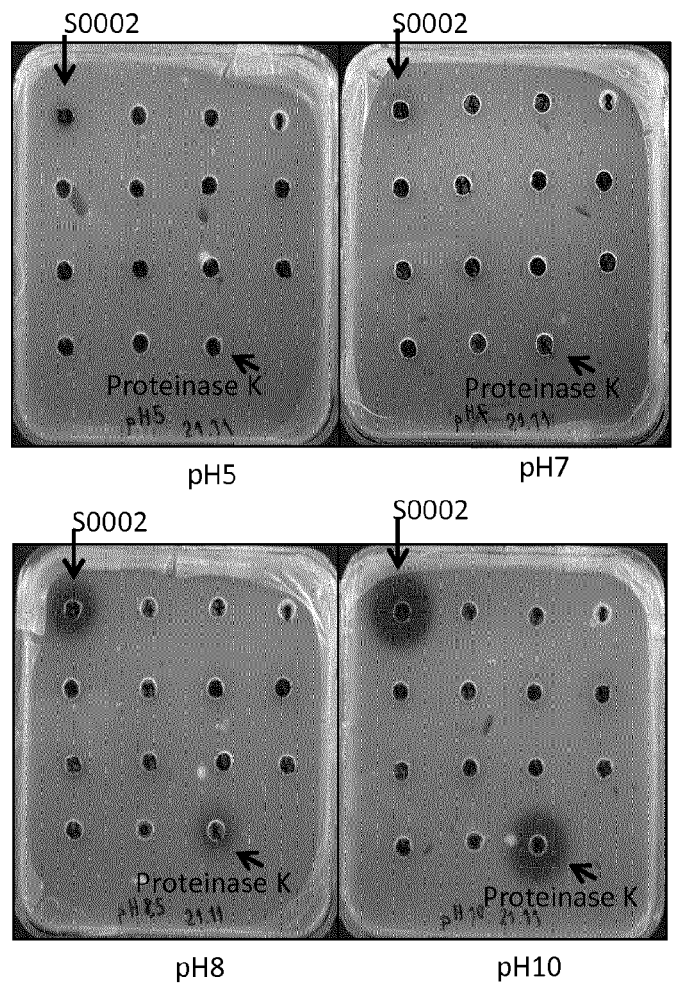

PLA-degrading activity of S0002 secreted enzymes was investigated and characterized. Recovered enzymes were tested for activity under different pH (pH5, pH7, pH8.5, and pH10) by the emulsified-PLLA agarose plate assay. Since proteinase K from *Tritirachium album* has been reported to have the ability to degrade PLA effectively [Williams D, 1981], proteinase K was included as a positive control in all experiments. As shown in FIG. 5, at pH5, neither S0002 secreted enzymes nor proteinase K displayed PLA-degradation activity. A slight clear-zone started to appear by S0002 secreted enzymes at pH7, it got more obvious at pH8.5, and the best clear-zone appeared at pH10. As for proteinase K, clear-zone appeared at pH8.5 and was the best at pH10. However, the clear-zone of proteinase K at pH8.5 was not as strong as the clear-zone of S0002 secreted enzymes. This result suggests that, secreted enzymes of S0002 may have better activity than proteinase K at pH8.5.

Temperature influence on PLA-degrading activity was also investigated by using the emulsified-PLA turbidity assay. Turbidity assay consists of the following method: emulsified PLA was prepared by emulsifing 0.5% PLA in $H_2O$ or 20 mM Tris-HCl pH 7. This emulsion was then diluted 6-fold with 120 mM Tris pH 8 to reach an absorbance value about 1 at OD 580 nm and final Tris concentration at 100 mM. Secreted enzymes were incubated with this diluted emulsion and the decrease in turbidity was monitored at OD 580 nm over time.

Figure 6:
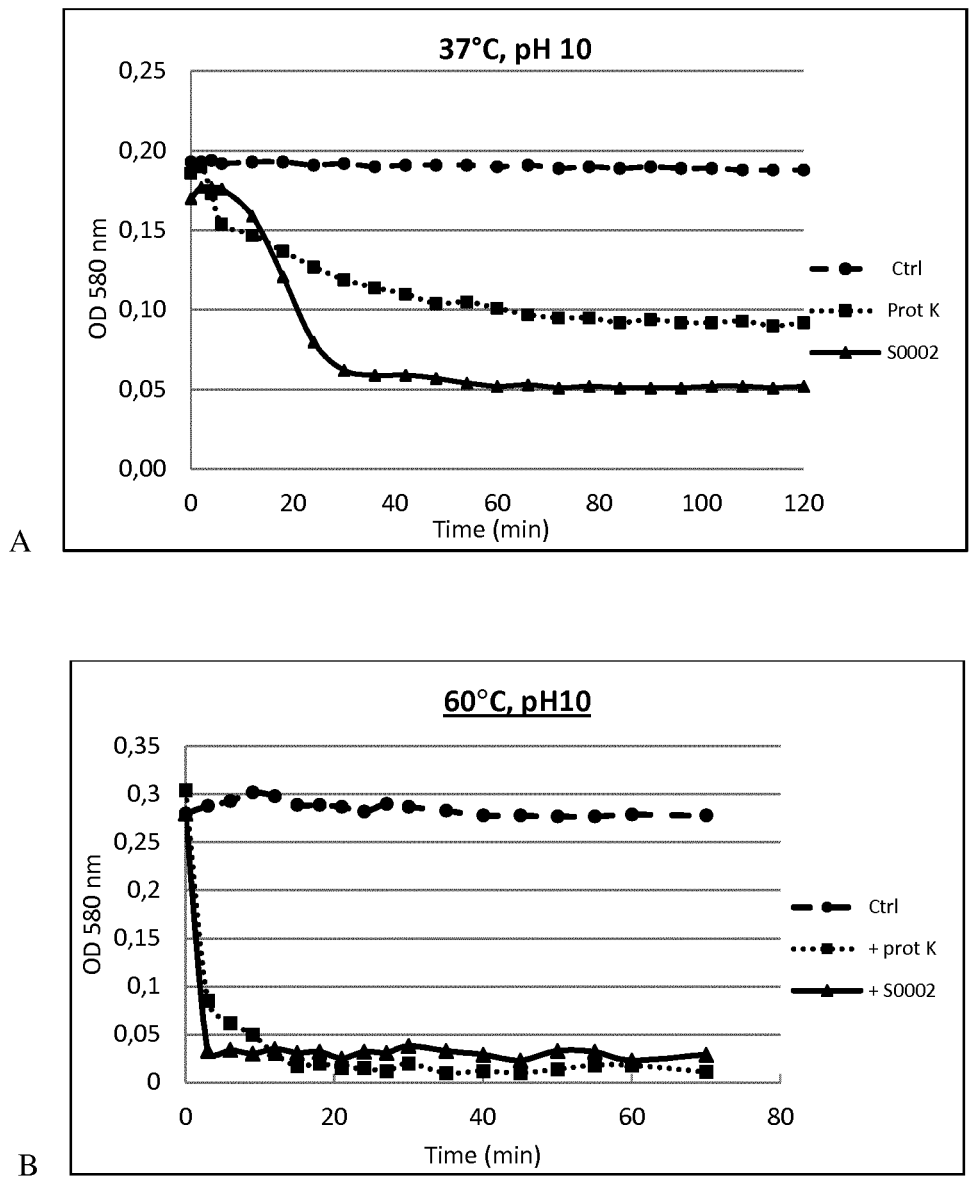

PLA-degrading activity was measured at 37° C. and 60° C. As shown in FIG. 6, both S0002 secreted enzymes and proteinase K could resist temperature at 60° C. and displayed similar PLA-degrading activity. Interestingly, at 37° C., S0002 secreted enzymes appeared to have better activity than proteinase K. One thing to keep in mind is that the glass transition temperature of PLA is around 55-60° C. Therefore, at 60° C., there are more amorphous PLA molecules and they may be more susceptible for enzyme degradation. Enzymes that are activated at a lower temperature (such as S0002 enzymes) have obvious advantage for practical use.

Example 3. Degradation of Polylactic Acid Semi-Crystalline Solid Materials

*Micromonospora* strain S0002's degrading activity and *Micromonospora* strain secreted enzymes' degrading activity were tested on high molecular weight and semi-crystalline PLA film (98% PLLA, 2% PDLA, Mw 129,500, Goodfellow SARL, Lille, France).

The GoodFellow PLA film was cut into 3 cm squares and weighted, sterilized in ethanol for overnight, dried in a laminar flow hood, and then added into cultures of S0002 or S0002 secreted enzymes reactions. After the incubation, film was repeatedly washed with 1% SDS and milliQ water, dried at 37° C., and then measured for weight loss. Degradation of films by S0002 secreted enzymes and by strain *Micromonospora* S0002 directly were both tested.

For S0002 secreted enzymes degradation, after incubation at 37° C. for 48 hours, the film was broken and had 17% weight loss. As for the negative control, there was neither obvious change of the film appearance nor weight loss (FIG. 7A).

Figure 7:
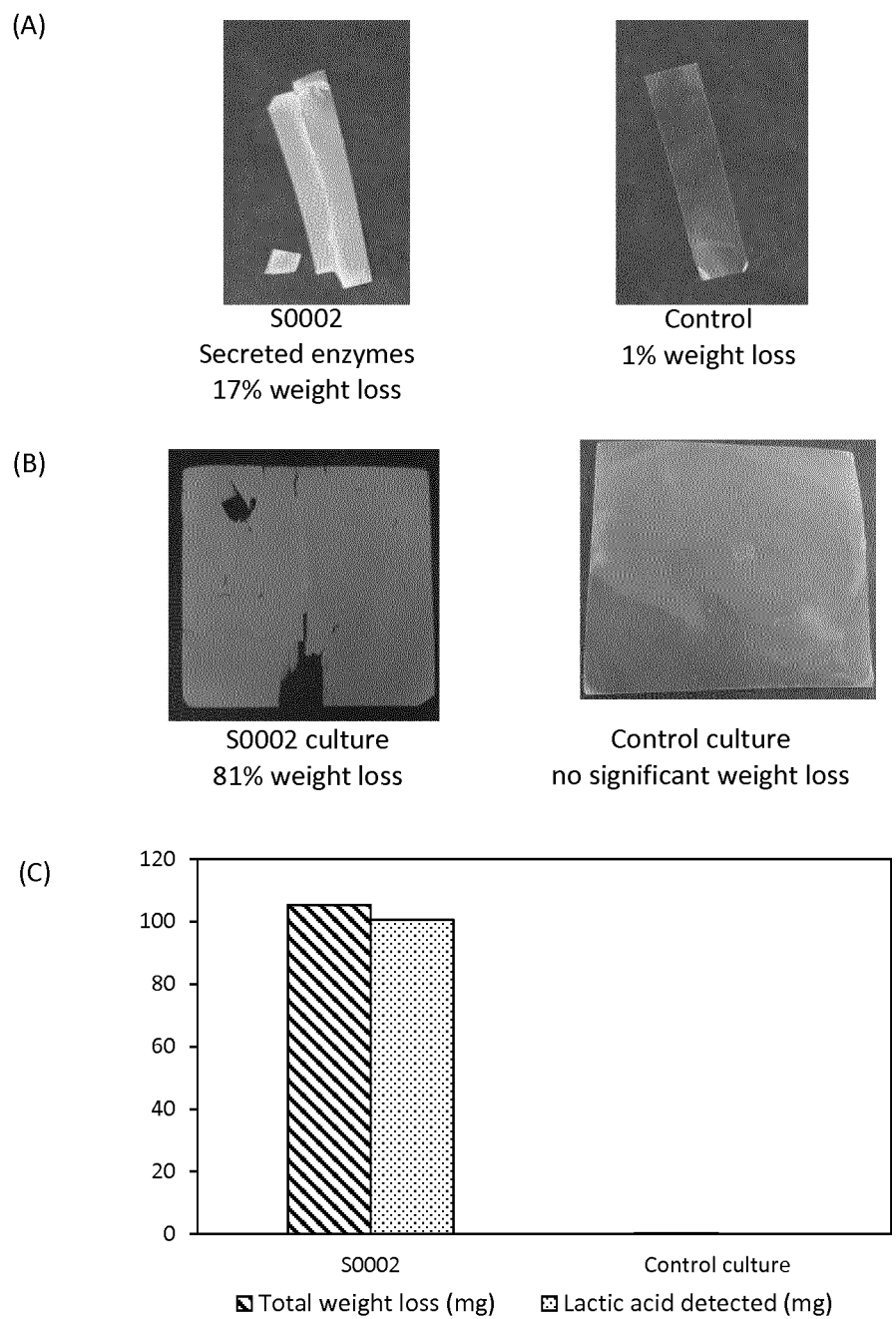

For direct degradation by the strain, after cultured with S0002 at 37° C. for 30 days, the film was not only thinner and broken, but also had 80.6% weight loss (FIG. 7B).

This result demonstrated that secreted enzyme(s) of S0002 and S0002 *Micromonospora* strain itself can degrade high molecular weight, semi-crystalline PLA film.

Example 4. Lactic Acid Recovery

The polypeptide of the invention can be used in recycling process of PLA where the recovery of lactic acid (the monomer of PLA) is an important step. Therefore, it is necessary to test whether lactic acid was generated.

Lactic acid generation during the degradation step was assessed. The culture supernatant from example 3 (*Micromonospora* S0002 strain cultured with high molecular weight, semi-crystalline PLA film) was collected and assayed for lactic acid content by using the Lactic acid assay kit (Megazyme, Wicklow, Ireland). As a result, the total lactic acid content in culture supernatant represented 95.4% of the film weight loss (FIG. 7C). This result suggests that *Micromonospora* S0002 strain of the invention can degrade high molecular weight, semi-crystalline PLA film into lactic acid, but do not consume lactic acid. Therefore, *Micromonospora* strain S0002 of the invention can be used for PLA recycling in order to recover lactic acid.

Figure 8:
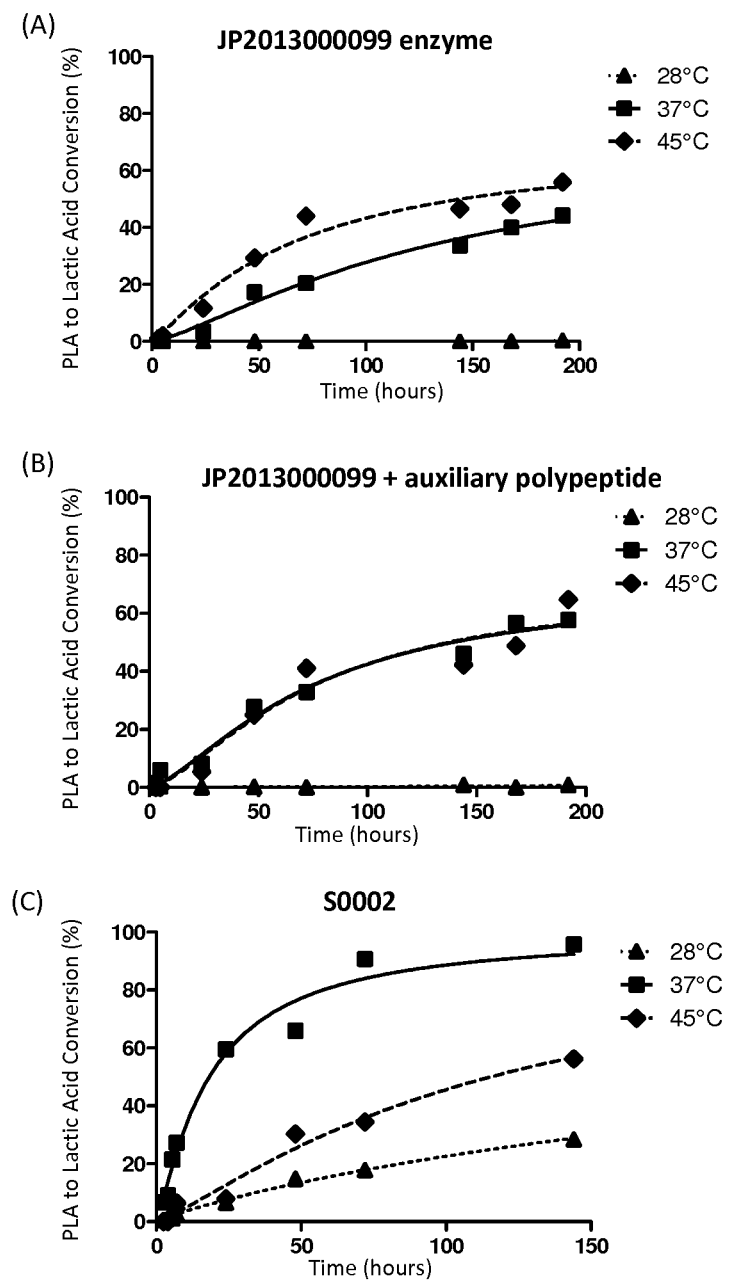
FIG. 8 illustrates the PLA-degrading activity (conversion of PLA into lactic acid) in culture supernatants at various temperatures (28° C., 37° C., and 45° C., pH 10) with various enzymes: (A) JP20130099 enzyme. (B) Chimera enzyme containing the JP2013000099 enzyme and an auxiliary peptide as set forth in SEQ ID No3 and (C) Enzyme of *Micromonospora* strain S0002.

Example 5. Advantage of the Auxiliary Polypeptide on Polyesterase Optimum Temperature The gene of the JP2013000099 enzyme has been synthesized, whose amino acid sequence is described in the patent application JP2013000099. Then a chimera of JP2013000099 enzyme with the auxiliary polypeptide has been constructed in order to investigate the role of the auxiliary polypeptide of polyesterase M2. PLA degradation assay was performed as follow: 100 mg of PLA powder and 750 µL of crude or concentrated culture supernatant were placed inside a dialysis bag (D9777, Sigma-Aldrich, St. Louis, Mo., USA). The bag was then dialyzed against 50 mL 0.1 M Tris buffer with stirring at the appropriate pH and temperature. Samples were withdrawn from the dialysis buffer at different time points and lactic acid content was measured (Lactic acid assay kit, Megazyme) following the manufacturer's protocol. Results have shown that the auxiliary polypeptide has no significantly effect on the pH profile of the JP2013000099 enzyme activity. Yet interestingly, the auxiliary polypeptide did change the temperature profile of the JP2013000099 enzyme activity. According to the results, the original JP2013000099 enzyme could only reach its maximal activity at 45° C. (FIG. 8A) whereas the chimera JP2013000099 enzyme/auxiliary polypeptide however, could already reach the same level of maximal activity at 37° C. (FIG. 8B), which is similar to S0002 (FIG. 8C).

The auxiliary polypeptide successfully improved the JP2013000099 enzyme by lowering the optimum temperature for activity. The auxiliary peptide increased the activity range of the JP2013000099 enzyme. This suggests that the auxiliary polypeptide may be a potential option for improvement of other enzymes.

Example 6. Degradation of Polyesters

Strain *Micromonospora* S0002 of the invention has been tested for its ability to degrade several kind of polyesters by using the "clear-zone" method.

Media that were used for this study are: R2 medium ([Reasoner D & Geldreich E, 1985]. One liter medium contains: 0.5 g yeast extract, 0.5 g proteose peptone, 0.5 g casamino acids, 0.5 g glucose, 0.5 g soluble starch, 0.3 g sodium pyruvate, 0.3 g $K_2HPO_4$, 0.05 g $MgSO_4.7H_2O$. When applicable, agar and/or polymers can be added as described in Example 1); Minimal medium for actinobacteria with the polymer of choice to serve as the sole carbon source. One liter medium contains: 2 g $KH_2PO_4$, 2.4 g $Na_2HPO_4$, 2 g $NH_4Cl$, 0.2 g $MgCl_2$, 1 mL trace elements solution M333, and 200 µL vitamin solution V7 (final pH 6.8-7.4). For one liter of M333 solution: 50 g $Na_2$-EDTA, 11 g $ZnSO_4.7H_2O$, 7.34 g $CaCl_2.2H_2O$, 2.5 g $MnCl_2.4H_2O$, 0.5 g $CoCl_2.6H_2O$, 0.5 g $(NH_4)_6Mo_2O_{24}.4H_2O$, 5 g $FeSO_4.7H_2O$, 0.2 g $CuSO_4.5H_2O$, and 11 g NaOH. For one liter of V7 solution: 2 mg biotin, 50 mg pyridoxamine, 10 mg thiamine HCl, 20 mg nicotinic acid, 5 mg calcium pantothenate, 20 mg vitamin B12, and 10 mg p-aminobenzoic acid.

Different substrates were tested. These polymers were tested with the clear-zone method: polymers were dissolved in dichloromethane and then emulsified in agar media.

PLLA powder (>99.5% L-PLA, <0.5% D-PLA, NaturePlast, Ifs, France)

PDLA powder (>99.5% D-PLA, <0.5% L-PLA, NaturePlast, Ifs, France)

PBS powder (PBE 003, NaturePlast, Ifs, France)

PHA powder (P(3HB-co-4HB), Metabolix, Cambridge, Mass., USA)

Figure 9:
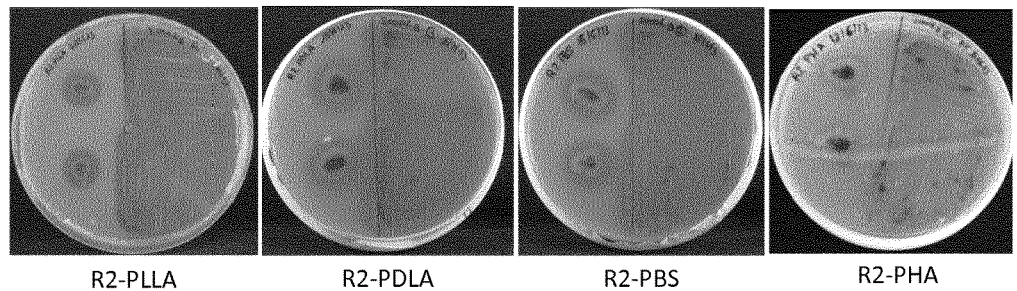
FIG. 9 shows that *Micromonospora* strain S0002 degrades poly L-lactic acid (R2-PLLA), poly D-lactic acid (R2-PDLA), polybutylene succinate (R2-PBS), and polyhydroxyalkanoate (R2-PHA) on R2 agar plates.

After 8-24 days, translucent "clear-zone" surrounding the colony on agar plates appeared reflecting the plastic degradation by the strain *Micromonospora* S0002 as showed in FIG. 9. S0002 has displayed degradation activities toward poly L-lactic acid (PLLA), poly D-lactic acid (PDLA), polybutylene succinate (PBS), and polyhydroxyalkanoate (PHA).

Example 7. Optimization of the Polyesterase Production from Culture Supernatants In order to improve the yield of polyesterase M2 production in S0002 culture supernatants, media of different compositions were assayed and compared, among which the RS medium (Rajasimman M & Subathra S, 2009), and the MMK medium (El-Bondkly & El-Gendy, 2010) supplemented or not with either $10\ g \cdot L^{-1}$ or $20\ g \cdot L^{-1}$ gelatin, which gave the most promising results. One liter of RS medium contains 3 g meat extract, 5 g yeast extract, 4 g $CaCO3$, 24 g soluble starch and 1 g glucose. MMK medium contains 0.5 g/L K2HPO4, 0.5 g/L KH2PO4, 1 g/L MgSO4.7H2O, 0.1 g/L CaCl2, 0.015 g/L FeSO4.7H2O, 0.005 g/L ZnSO4.7H2O, 0.3 g/L NaCl (pH 8).

The conversion of PLA into Lactic Acid was performed at 37° C. and pH 10, using crude supernatants from S0002, preliminary grown under different conditions, i. e. after 20 days in RS medium (RS), 2 days in MMK medium supplemented (K1-2d and K2-2d) or not (M) with $10\ g \cdot L^{-1}$ (K1-2d) or $20\ g \cdot L^{-1}$ (K2-2d) gelatin and 4 days in MMK medium supplemented with $20\ g \cdot L^{-1}$ gelatin (K2-4d). After this period of time, PLA degradation was assayed from crude supernatants, as already described in Example 5. Powder from PLLA NaturePlast (500 µm) was used as the substrate.

As shown in FIG. 10, the best medium identified so far for polyesterase M2 production corresponds to a MMK medium supplemented with gelatin: up to 80% conversion of PLA to lactic acid was obtained, after a 24 h incubation with a crude supernatant from a 4-day culture in MMK+2% gelatin.

Example 8. Lactic Acid Production from Commercial PLA-Containing Material

The polyesterase M2 may advantageously be used for the recycling of PLA-containing material (commercial objects) to Lactic Acid (LA). In order to evaluate the potency of polyesterase M2 in such a process, conversion of PLA to LA from commercial objects was assessed using the method described in Example 5 at 37° C. and pH 10 using crude supernatants from S0002, preliminary grown for 4 days in MMK medium supplemented with $20\ g \cdot L^{-1}$ gelatin. In this aim, PLA powders (500 µm) were produced from either:

PLA-based Cutlery

PLA-based shrink-wrapped trays

PLA-based shrink-wraps

PLA-based beakers

PLLA powder (>99.5% L-PLA, <0.5% D-PLA, NaturePlast, Ifs, France)

As shown, LA has be obtained from powders of all the commercial objects tested in this study, albeit with different yields and rates (FIG. 11). These data clearly demonstrate that S0002 supernatant can be used for the efficient recycling of commercial objects containing PLA.

---

The invention claimed is:

1. A nucleic acid operably linked to a heterologous promoter, said nucleic acid encoding a polypeptide having a polyester degrading activity and having at least 90% identity to the full length amino acid sequence of SEQ ID NO: 1.

2. An expression cassette comprising the nucleic acid of claim 1.

3. A vector comprising the nucleic acid of claim 1.

4. A recombinant cell containing a nucleic acid of claim 1.

5. A method of producing a polypeptide, comprising:
(i) culturing a recombinant cell of claim 4 to express the polypeptide, said polypeptide having a polyester degrading activity and having at least 90% identity to the full length amino acid sequence of SEQ ID NO: 1; and
(ii) recovering the expressed polypeptide from the culture supernatant or the cells.

6. A method for degrading a polyester containing material, comprising the step of exposing the polyester containing material to a polypeptide having a polyester degrading activity, said polypeptide comprising an amino acid sequence having at least 90% sequence identity to the full length amino acid sequence of SEQ ID NO: 1.

7. The method of claim 6, wherein at least one polyester of the polyester containing material is depolymerized up to monomers and/or oligomers.

8. The method of claim 6, comprising a pretreatment step of the polyester containing material to submit the polyester containing material to at least one modification selected from mechanical modification, physical modification, chemical modification, biological modification.

9. The method of claim 6, comprising a subsequent step of b) recovering the resulting monomers and/or oligomers.

10. A plastic compound containing a polypeptide having a polyester degrading activity and comprising at least 90% sequence identity to the full length amino acid sequence of SEQ ID NO: 1, and at least one polyester.

11. A process for producing a plastic compound, wherein at least one polyester and a polypeptide having a polyester degrading activity, said polypeptide comprising an amino acid sequence comprising at least 90% sequence identity to the full length amino acid sequence of SEQ ID NO: 1 are mixed at a temperature at which the polyester is in a partially or totally molten state.

12. The plastic compound of claim 10, wherein the polypeptide further comprises, at the C-terminal end or at the N-terminal end of said amino acid sequence having at least 90% sequence identity to the full length amino acid sequence of SEQ ID NO: 1, an amino acid sequence, that has at least 75% sequence identity to the full length amino acid sequence of SEQ ID NO: 3.

13. The process for preparing a plastic compound of claim 11, wherein the step of mixing a polyester with the polypeptide is performed at a temperature at which the polyester is in a partially or totally molten state.

14. The process for preparing a plastic compound of claim 13, wherein the step of mixing is performed by extrusion.

15. The process for preparing a plastic compound of claim 11, wherein the polyester is selected from the group consisting of PLA, PBS and PHAs.

16. The process for preparing a plastic compound of claim 15, wherein the polyester is PLA and the step of mixing is performed at a temperature at which PLA is in a partially or totally molten state.

17. The method of claim 6, wherein the polyester is PLA and the polypeptide has a PLA degrading activity.

18. The method of claim 6, wherein the polypeptide further comprises, at the C-terminal end or at the N-terminal end of said amino acid sequence having at least 90% sequence identity to the full length amino acid sequence of SEQ ID NO: 1, an amino acid sequence that has at least 75% sequence identity to the full length amino acid sequence of SEQ ID NO: 3.

19. The method of claim 6, wherein the polypeptide having a polyester degrading activity comprises an amino acid sequence having at least 95% sequence identity to the full length amino acid sequence of SEQ ID NO: 1.

20. The plastic compound of claim 10, wherein the polypeptide having a polyester degrading activity comprises an amino acid sequence having at least 95% sequence identity to the full length amino acid sequence of SEQ ID NO: 1.

21. The process of claim 11, wherein the polypeptide having a polyester degrading activity comprises an amino acid sequence having at least 95% sequence identity to the full length amino acid sequence of SEQ ID NO: 1.

* * * * *